(12) United States Patent
McBride et al.

(10) Patent No.: US 7,700,373 B2
(45) Date of Patent: Apr. 20, 2010

(54) ASSAY METHOD AND APPARATUS

(75) Inventors: Jeffrey D. McBride, London (GB); Francis Guy Gabriel, London (GB); Peter J. Delves, London (GB); John L. A. Fordham, London (GB); Ian A. Cree, London (GB); Keith Rawson, Cambridgeshire (GB)

(73) Assignee: Nalia Systems Ltd., Cambridge (GB)

( * ) Notice: Subject to any disclaimer, the term of this patent is extended or adjusted under 35 U.S.C. 154(b) by 817 days.

(21) Appl. No.: 10/557,563

(22) PCT Filed: May 21, 2004

(86) PCT No.: PCT/GB2004/002203

§ 371 (c)(1),
(2), (4) Date: Nov. 24, 2006

(87) PCT Pub. No.: WO2004/103939

PCT Pub. Date: Dec. 2, 2004

(65) Prior Publication Data

US 2007/0184494 A1    Aug. 9, 2007

(30) Foreign Application Priority Data

May 22, 2003    (GB) .................................. 0311902.1

(51) Int. Cl.
    *G01N 33/543*    (2006.01)

(52) U.S. Cl. ........................... 436/518; 422/56; 422/57; 422/58; 435/287.1; 435/287.2; 435/288.7; 435/810; 436/805; 436/810

(58) Field of Classification Search ............... 422/56, 422/57, 58; 435/287.1, 287.2, 288.7, 810; 436/518, 805, 810
See application file for complete search history.

(56) References Cited

U.S. PATENT DOCUMENTS

| | | | |
|---|---|---|---|
| 4,493,815 A | 1/1985 | Fernwood et al. | ........... 422/101 |
| 5,022,411 A | 6/1991 | Guirguis | ...................... 128/771 |
| 5,030,555 A * | 7/1991 | Clemmons | .................... 435/5 |
| 5,149,626 A * | 9/1992 | Fleming | ...................... 435/7.9 |

(Continued)

FOREIGN PATENT DOCUMENTS

EP    0 339 769 A1    11/1989

(Continued)

OTHER PUBLICATIONS

MultiScreen Methods: Guidelines for Bioassays on MultiScreen Plates: Protein Binding and Cell Loading; 1994, 1997.

(Continued)

*Primary Examiner*—Christopher L Chin
(74) *Attorney, Agent, or Firm*—Renner, Otto, Boisselle & Sklar, LLP

(57) ABSTRACT

The present invention relates to an apparatus for use in an assay comprising: (a) at least one first receptacle comprising a fluid inlet and a fluid outlet, (b) a porous membrane, and (c) at least one analyte-specific binding agent, characterised in that said at least one analyte-specific binding agent is immobilised on the underside of said porous membrane relative to the fluid inlet; and to methods of performing said assay.

51 Claims, 15 Drawing Sheets

U.S. PATENT DOCUMENTS

| | | | |
|---|---|---|---|
| 5,942,442 A | 8/1999 | Rosen et al. | 436/501 |
| 5,976,824 A | 11/1999 | Gordon | 435/29 |
| 2003/0049862 A1 | 3/2003 | He et al. | 436/180 |

FOREIGN PATENT DOCUMENTS

| | | |
|---|---|---|
| EP | 0 508 010 A1 | 10/1992 |
| WO | 00/60116 | 10/2000 |
| WO | 02/08727 A1 | 1/2002 |
| WO | 03/005013 A1 | 1/2003 |
| WO | 03/034026 A2 | 4/2003 |

OTHER PUBLICATIONS

International Search Report and Written Opinion; Application No. PCT/GB2004/002203; mailed Mar. 30, 2005.

* cited by examiner

ASSAY METHOD AND APPARATUS

FIELD OF THE INVENTION

The present invention relates to an apparatus for use in assays for detecting and/or quantifying the presence of one or more analytes in a sample and to methods of performing such assays.

BACKGROUND OF THE INVENTION

Numerous apparatus and methods for use in detecting and/or quantifying the presence of analytes in a sample have been developed. Such tests can be used, for example, to define the exact composition of a sample (qualitative assay) or to determine the precise amount or concentration of any given analyte in that sample (quantitative assay). Practical applications of such tests include environmental monitoring, medical research and analysis.

Common methods in the field of medical research and analysis include polypeptide and polynucleotide assays.

Examples of polypeptide assays include immunoassays, ELISA and Western blotting, all of which are based on the principle of antibody/antigen interaction. Immunoassays, for example, are usually carried out in multi-well plates. However, using such apparatus means that only a single analyte can be tested in each well. Assays for testing large numbers of compounds simultaneously have been developed. However, to date, these have mostly been limited to polynucleotide assays.

Polynucleotide assays, which are based on hybridisation between complementary nucleic acid sequences, include Northern and Southern blots, PCR and, more recently, micro-arrays. While micro-arrays allow up to several thousand compounds to be tested simultaneously, they have the disadvantage of generally requiring all analytes to be tested against a single sample.

Current polypeptide and polynucleotide assays are therefore restrictive in terms of the actual number of individual binding assays that can be performed at any one time. In addition, current methods are often not capable of detecting small amounts of a test substance. The most recognised explanation for this is the problem of background staining whereby irrelevant analytes bind non-specifically and particulate matter prevents analyte-specific binding and, after completion of an assay, often remains on the test surface thereby interfering with specific signalling and the clarity and reliability of any readouts.

There is therefore a need to develop improved methods for performing such assays. The present invention seeks to overcome at least some of the aforementioned problems, and seeks to provide an assay method, and apparatus for use therein, which is precise, reproducible, accurate, sensitive and specific.

STATEMENTS OF THE INVENTION

The present invention relates to assay methods and apparatus for reliably and efficiently detecting and/or quantifying the presence (or absence) of one or more analytes in a sample.

In a first aspect of the present invention, there is provided an apparatus for use in an assay for an analyte comprising:

(a) at least one first receptacle comprising a fluid inlet and a fluid outlet;

(b) a porous membrane, such as a membrane positioned at the fluid outlet; and (c) at least one analyte-specific binding agent, characterised in that said at least one analyte-specific binding agent is immobilised in a spot on the underside of said porous membrane relative to the fluid inlet.

The porous membrane should be porous to the analyte of interest.

By immobilising the analyte-specific binding agents on the underside of a membrane positioned at the base of a receptacle, background staining that could otherwise interfere with the reliability and/or specificity of results obtained may be reduced. In addition, by moving the reaction zone to the outside of the receptacle, generation and analysis of images will be facilitated, allowing, in particular, detection and/or imaging means to be included as part of a compact apparatus (whereas they would normally have to be provided separately). The porous membrane also allows for partial removal of non-specific binding analytes on the upper surface of the porous membrane and the removal of particulate matter from a sample before it is brought into contact with any analyte-specific binding agents which could otherwise reduce non-specific binding. Similarly, subsequent reagents employed for detection of binding agent/analyte interaction may be filtered. The provision of filtering means other than the porous membrane is not excluded.

It will be appreciated from the previous paragraph that the porous membrane can be considered as having an upper surface or region for filtering a sample before it is brought into contact with the analyte-specific binding agent. This upper surface or region can be considered as being directly above the analyte-specific binding agent. Typically this upper surface or region contains no analyte-specific binding agent.

It is a preferred embodiment of the present invention that a plurality of analyte-specific binding agents be bound to the membrane (in the form of a microarray, for example). By placing the analyte-specific binding agents on the outside of the receptacle, the reaction zone will be more accessible to the array forming process, thereby allowing for a greater number of analyte-specific binding agents to be immobilised on each membrane, since, for example, the walls of the receptacle may partially obstruct the pins or jet device used for deposition of analyte-specific binding agents.

It should also be noted that, whereas microarrays have previously been largely limited to polynucleotide analyte-specific binding agents, the present invention allows for both polynucleotide and polypeptide analyte-specific binding agents to be employed (i.e. combining microarrays and general ligand binding assays, such as immunoassays).

In one embodiment, the apparatus of the present invention comprises a plurality of receptacles, each of which preferably comprises an array of analyte-specific binding agents. This will allow for a greater number of compounds to be tested in considerably less time than traditionally expected. In particular, the present invention provides a method of carrying out a large number of microarray assays simultaneously (i.e. one per well of a multi-well plate), preferably in a complete, automated process.

Preferably, the apparatus of the invention comprises a plurality of first receptacles in the form of a multi-well plate (e.g. a 96-, 384- or 1536-well plate). According to one embodiment, a plurality of analyte-specific binding agents is immobilised on the porous membrane of the or each well, preferably in the form of an array (such as a microarray). At least one control analyte-specific binding agent may be included amongst the array of binding agents.

Analyte-specific binding agents according to the invention may include polynucleotide probes (such as ESTs), polypeptide probes (such as antibodies or fragments thereof, cell surface receptors or enzymes) or any other type of chemical compound which has the ability to be associated with the target analyte. They may be immobilised directly or indirectly onto the porous membrane.

Further components of the apparatus of the invention may include:

1. One or more second receptacles whereby the or each first receptacle is positioned at least in part in a second receptacle such that said second receptacle may collect liquid from the fluid outlet of said first receptacle, the porous membrane of which may thereby be submerged.

2. One or more additional porous membranes positioned within said at least one first receptacle such that membrane pore size gradually decreases from fluid inlet to fluid outlet.

3. A means for drawing liquid from the at least one first receptacle through the fluid outlet. According to one embodiment, said means may comprise a vacuum pump. According to other embodiments, the means may comprise absorbence, positive displacement or centrifugal filtration.

4. A means for detecting binding of an analyte to the binding agent. According to one embodiment, said detecting means is selected from fluorimetric, chemiluminescent, radiochemical and colourimetric means. The detecting means preferably comprises a photometric device (such as a luminometer) capable of detecting and/or quantifying light emitted from porous membrane. Even more preferably, the detecting means may comprise imaging means, such as a camera or scanner. Imaging means can be included either in addition or alternatively to other detecting means.

According to a second aspect of the present invention, there is provided an apparatus for use in an assay comprising a plurality of first receptacles in the form of a multi-well plate (such as a 96-, 384- or 1536-well plate), characterised in that each receptacle comprises an array (preferably a microarray) of immobilised analyte-specific binding agents. As above, at least one control probe may be included amongst the array of binding agents.

The analyte-specific binding agents, according to the second aspect of the present invention, may be directly or indirectly immobilised onto a surface of said first receptacle. Preferably, said surface is a porous membrane which serves as a fluid outlet for the receptacle. Even more preferably, the analyte-specific binding agents are immobilised onto the underside of said porous membrane.

Further components of the apparatus according to the second aspect of the present invention may include any of (1)-(4) as listed above, adapted as necessary.

According to a third aspect of the present invention, there is provided a method of detecting an analyte comprising:

(a) providing an apparatus according the invention (and as described above);

(b) loading a sample to be tested into the or at least one of the receptacles; and (c) detecting binding of the analyte to the analyte-specific binding agent(s).

According to one embodiment, said method may further comprise the step, between (b) and (c), of actively drawing liquid from the receptacle through the fluid outlet, with the use, for example, of a vacuum pump.

The sample may be, for example, a biological or environmental sample and may preferably include a detectable label, such as an enzyme, a fluorescent label or a radiolabel.

Detecting binding of the analyte(s) to the one or more analyte-specific binding agents in step (c) may be achieved using any one of fluorimetric means, chemiluminescent means, radiochemical means, colourimetric means, etc. depending of course on the nature of the label used. Preferably, binding is detected using a photometric device (such as a luminometer) capable of detecting and/or quantifying light emissions.

In a preferred embodiment, step (c) of the above described method is followed or replaced by imaging to individually detect and/or quantify light emissions from each area of binding agent immobilisation (said area being referred to herein as a "spot").

In a further embodiment, if the apparatus used in accordance with this method has more than one receptacle, a different sample is loaded to each receptacle.

In another aspect of the invention, there is provided a porous membrane having at least one analyte-specific binding agent immobilised on one side thereof. In use this side is the underside relative to a fluid inlet of the apparatus defined herein.

In a further aspect of the invention, there is provided a kit for use in a method of detecting an analyte, the kit comprising a porous membrane having at least one analyte-specific binding agent immobilised on one side thereof and at least one reagent for detecting binding of an analyte to the at least one analyte-specific binding agent.

DETAILED DESCRIPTION OF THE FIGURES

Figure 1A:
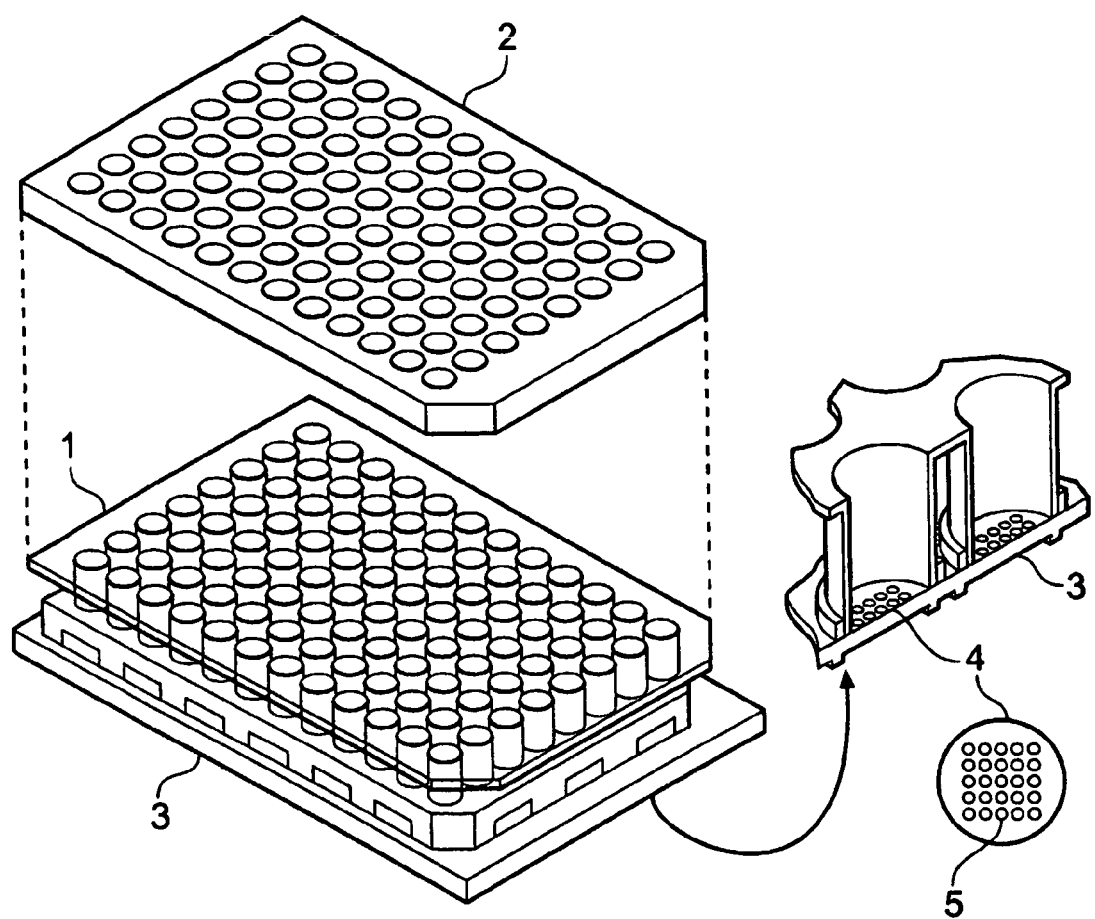
FIG. 1 shows a filtration multiwell microarray assembly according to the present invention and in which (A) is a 3D representation and (B) is a cross-sectional view.
Figure 1B:
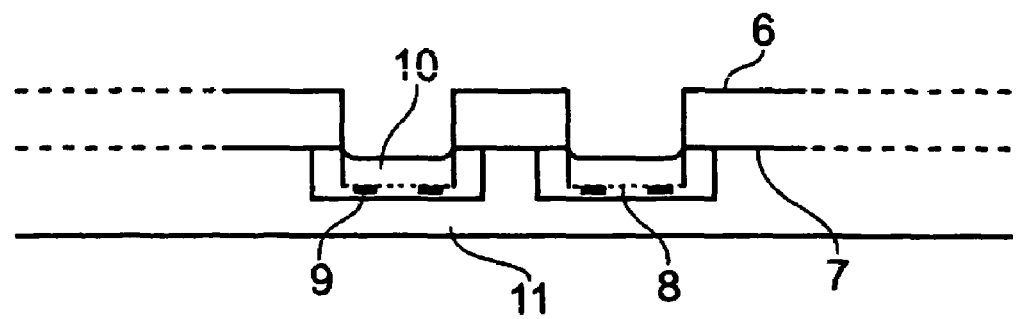
Figure 2:
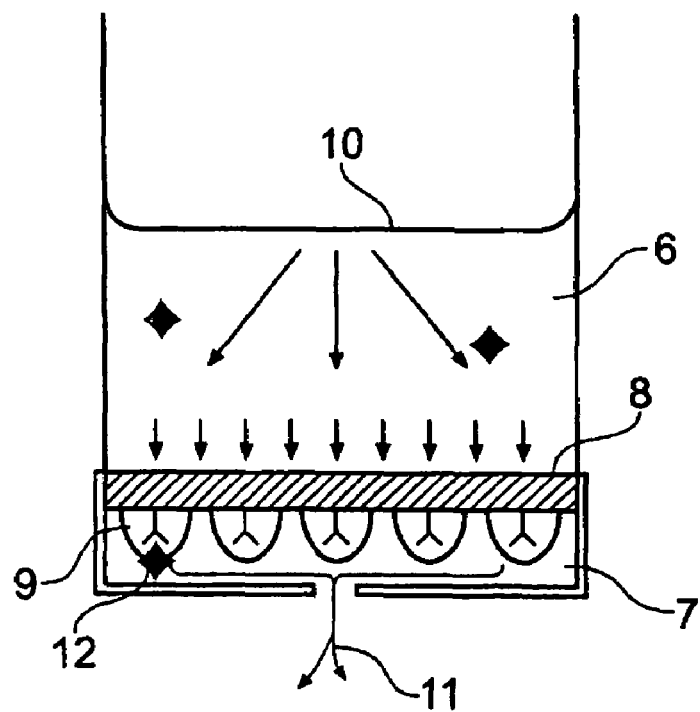
FIG. 2 shows a schematic representation of an embodiment of a filtration multiwell microarray assay of the present invention.

In more detail:

In these FIGS. 1A, 1B and 2—(1) represents a well plate, such as a 96-well plate, (2) is a cover, (3) is an underdrain, (4) is a filter, (5) shows the array, under-filter, (6) is receptacle 1, (7) is receptacle 2, (8) is a porous membrane, (9) is an analyte binding spot on the underside of the membrane; each spot containing a given probe(s), (10) is an analyte solution, (11) is a means to draw sample through the membrane, such as a vacuum, positive pressure or centrifugal force, and (12) is the analyte.

Figure 4:
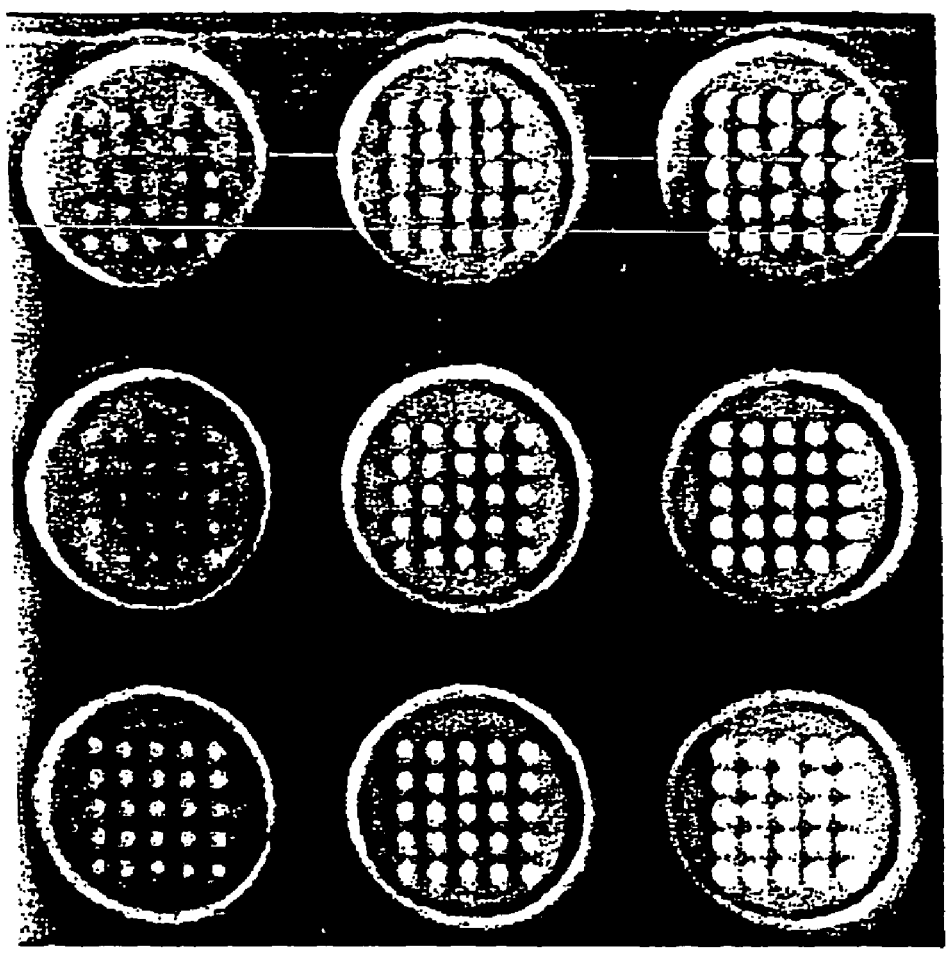
FIG. 4 is a representative image of well-arrays used in the construction of the standard curves of the graphs shown in FIGS. 5 and 6.

In FIG. 4—from left to right, top to bottom, thyroglobulin as probe spots were incubated with 100, 1000, 3000, 50, 750, 1500, 300, 1260, 7500 IU anti-thyroglobulin solutions. CCD-FDI exposure time of six seconds (FDI=fast digital imager).

Figure 5:
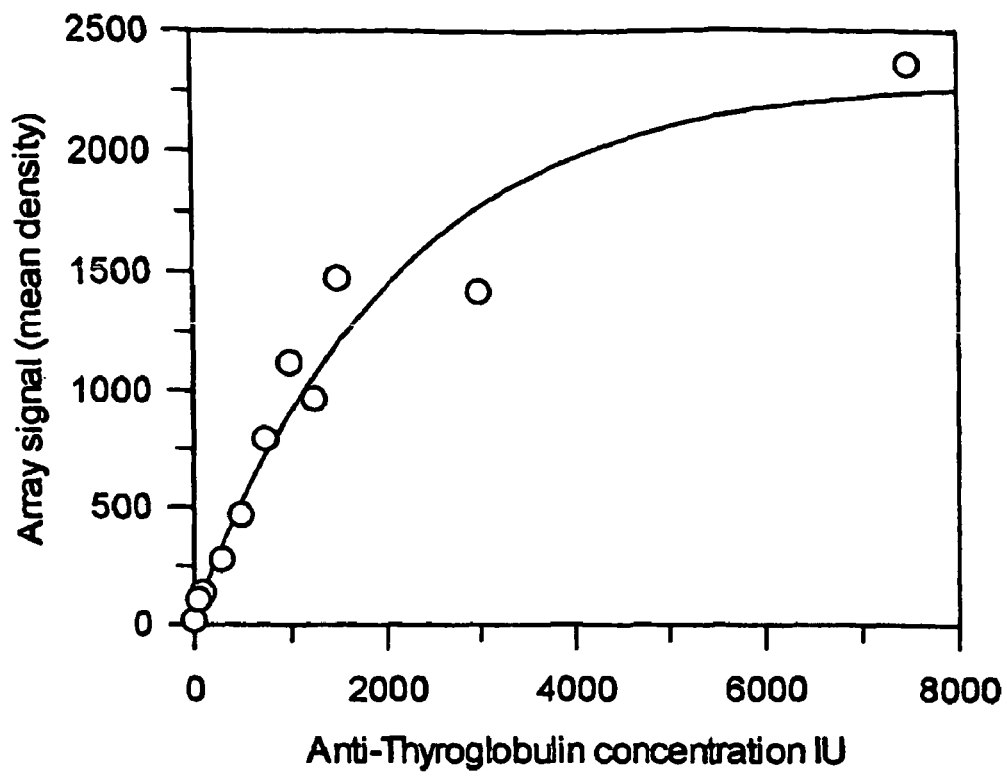
FIGS. 5 and 6 show calibration curves generated in accordance with Example 1.
Figure 6:
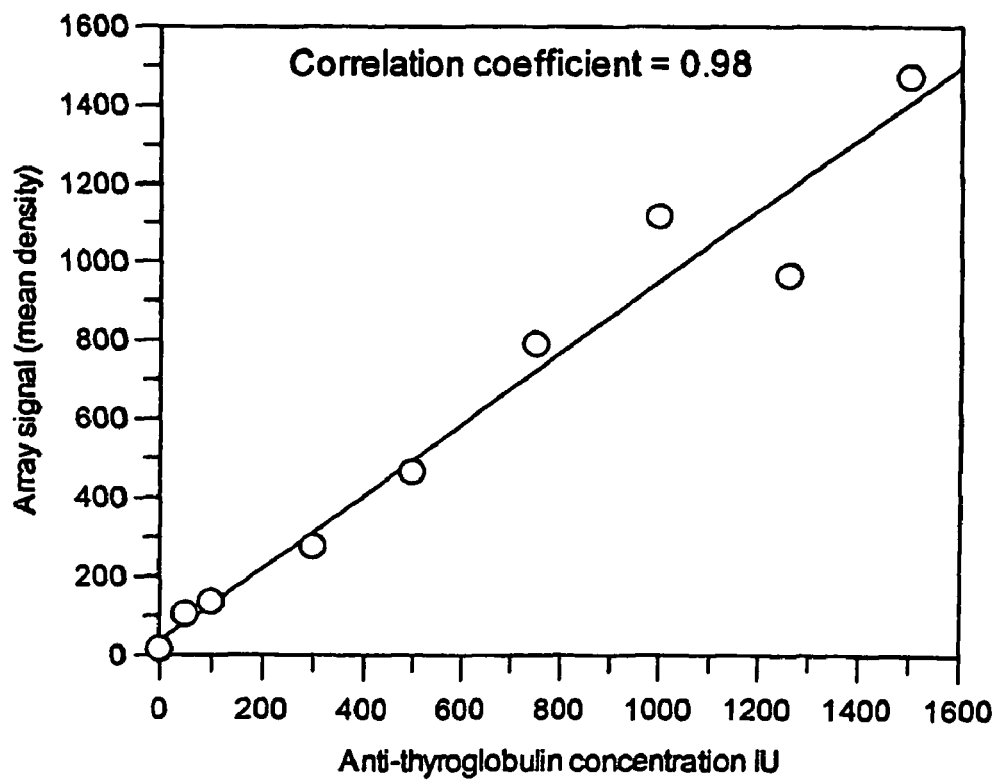

FIGS. 5 and 6—are calibration curves generated by incubation of standard anti-thyroglobulin solutions with immobilised thyroglobulin as capture probe. Array signal is the mean density of the array signal following a six second exposure time.

Figure 7:
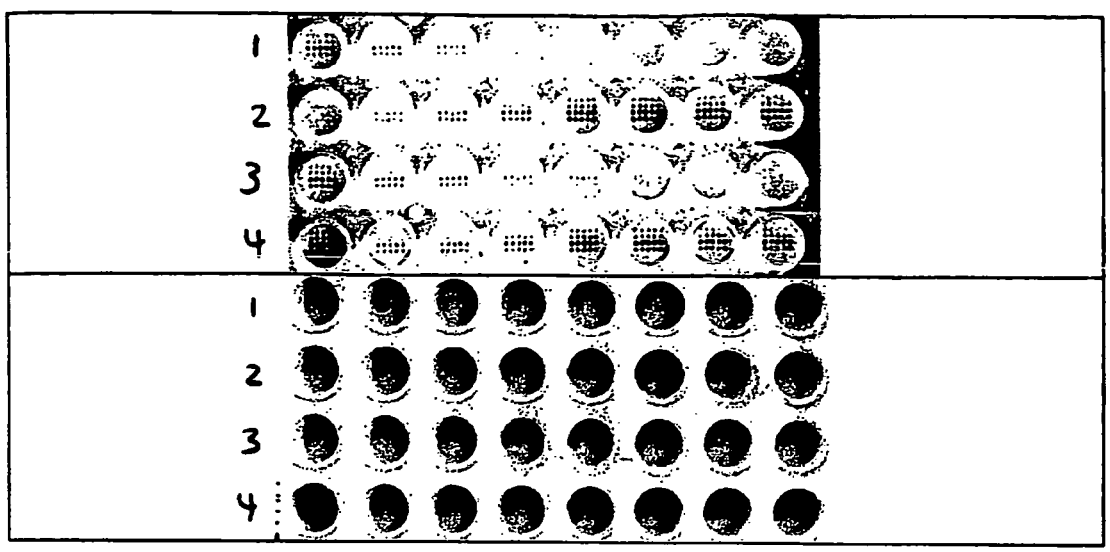
FIG. 7 shows the results of a filtration microarray assay in accordance with the present invention and Example 2.

FIG. 7—Analysis of arrays using colourimetric reagents. The lower half of FIG. 7 reveals that the major part of the serum background is filtered out on the upper surface. The 4 wells to the right of rows 2 and 4 are patient sera. Rows 2 and 4 have been stained with 4-Cl—N/DAB, the lower two rows, 3 and 4, with metal enhanced DAB.

Within well zones, the spot rows comprise 12.5 µg, 25 µg, 100 µg, 50 µg/mL Tg and buffer as probes from top to bottom.

Wells in rows 1 and 3 have been incubated with standardised anti-thyroglobulin solutions. From left to right, each well has been incubated with 1000, 750, 500, 300, 200, 100, 50 and 0 IU anti-thyroglobulin.

Rows 2 and 4 have been incubated with standardised anti-thyroglobulin solutions or patient sera. From left to right, 1260, 3000, 5000, 7500 IU standardised anti-thyroglobulin, positive patient serum A (greater than 10,000 IU) diluted 1/800, 1/1600 and 1/3200, positive patient serum B (~2560 IU) diluted 7.5 times.

Note, the upper image has been flipped such that wells correspond to the lower image. Standard curves given in FIGS. 8 and 9.

Figure 8:
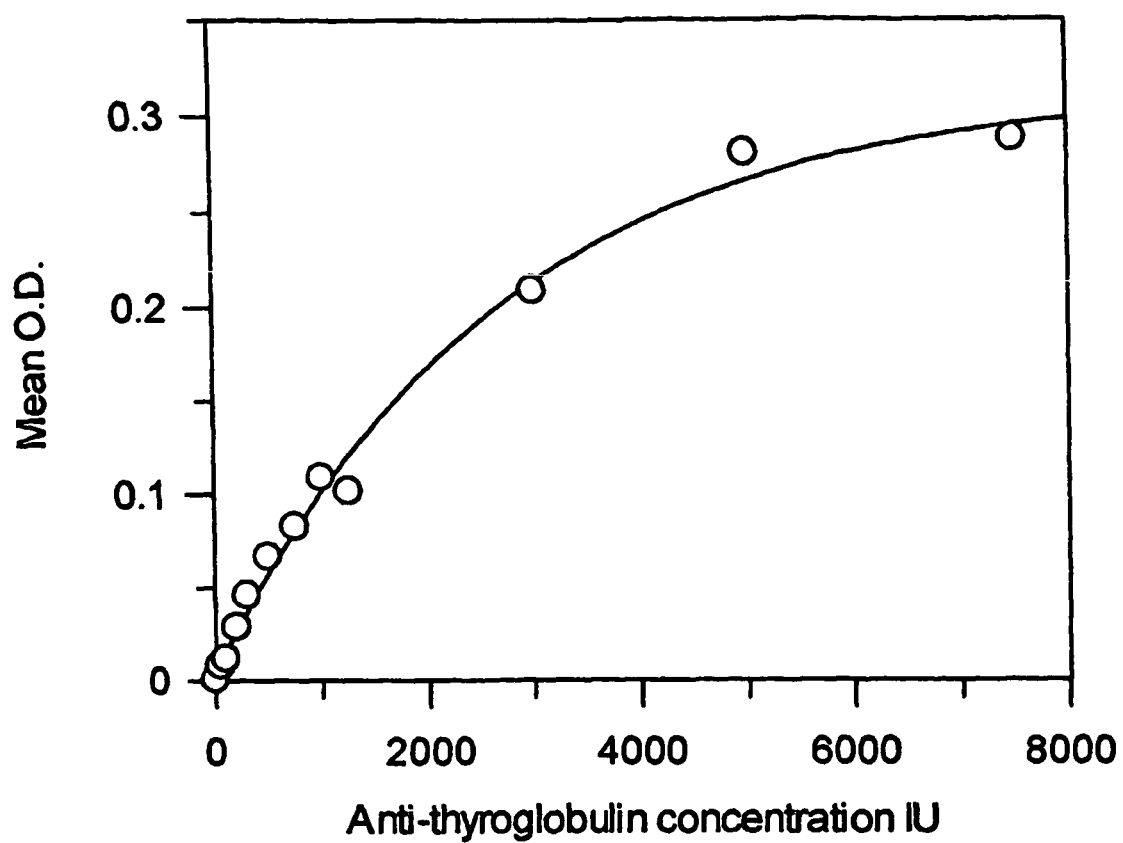
FIGS. 8 to 11 show calibration curves generated in accordance with Example 2.
Figure 9:
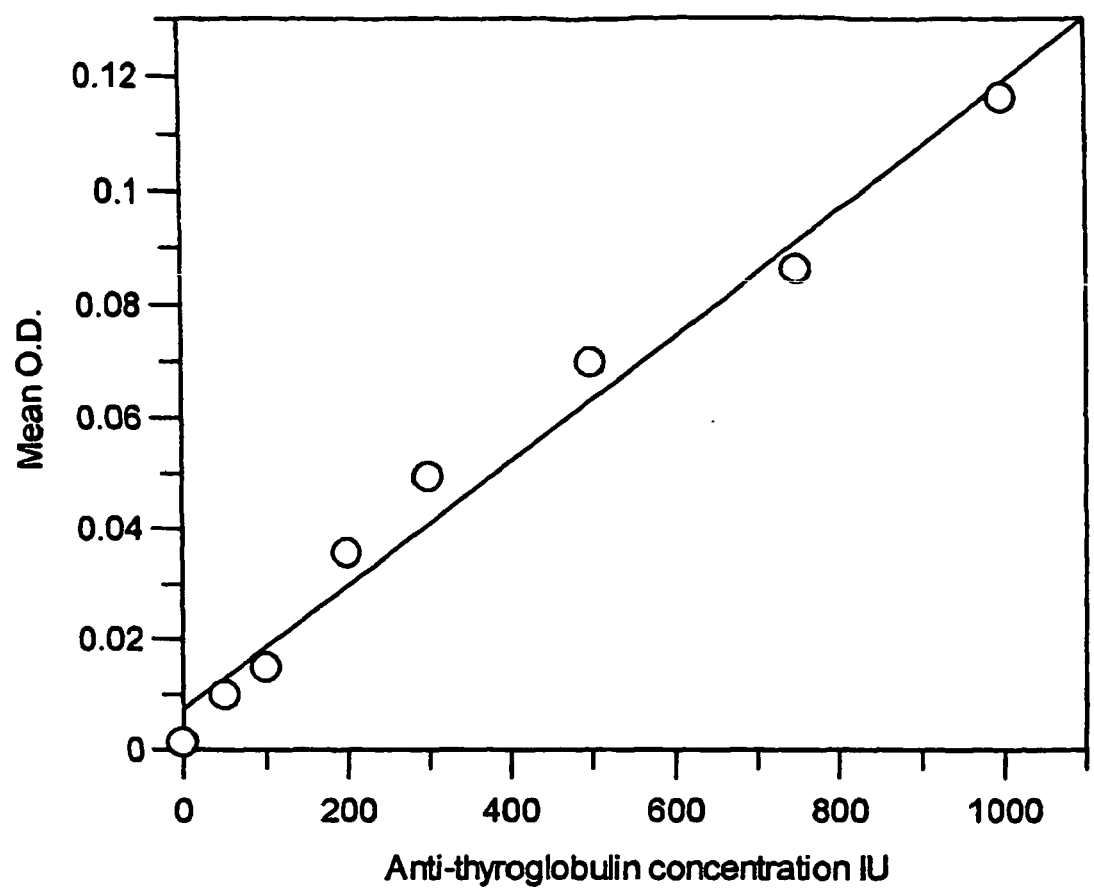

FIGS. 8 and 9—are anti-thyroglobulin calibration curve's generated using 4Cl—N/DAB as HRP substrate.

Figure 10:
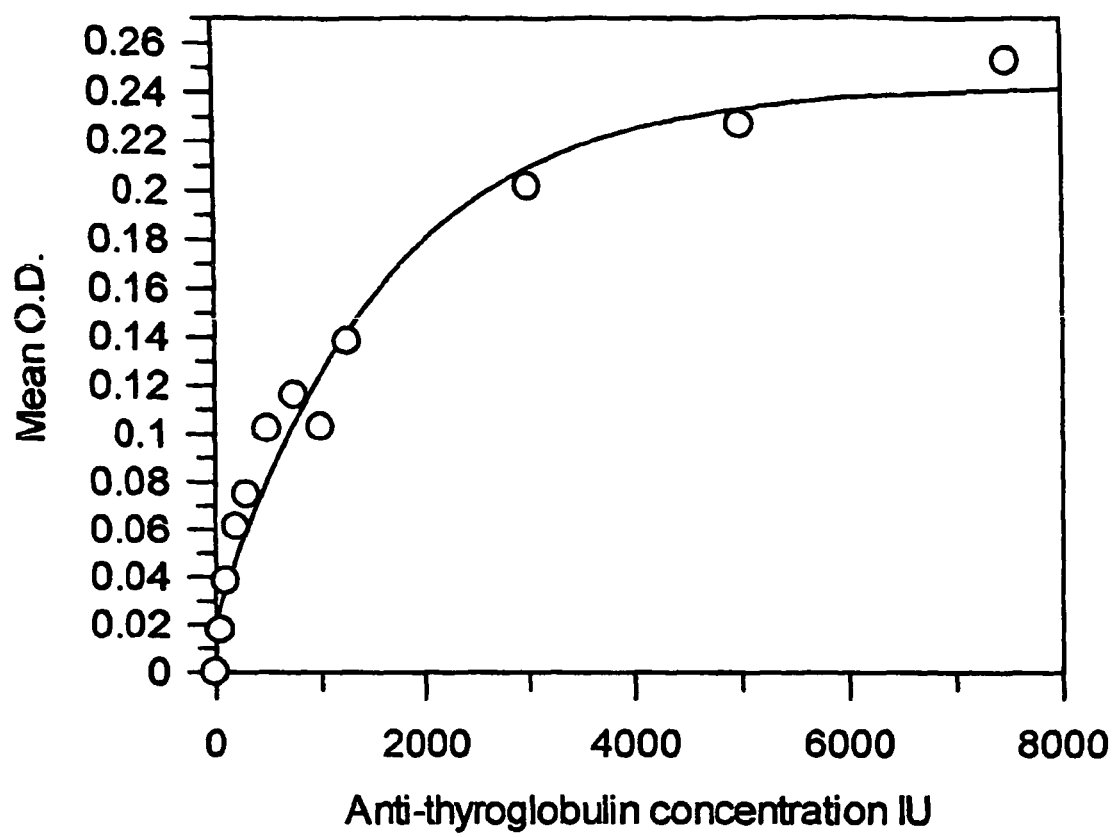
Figure 11:
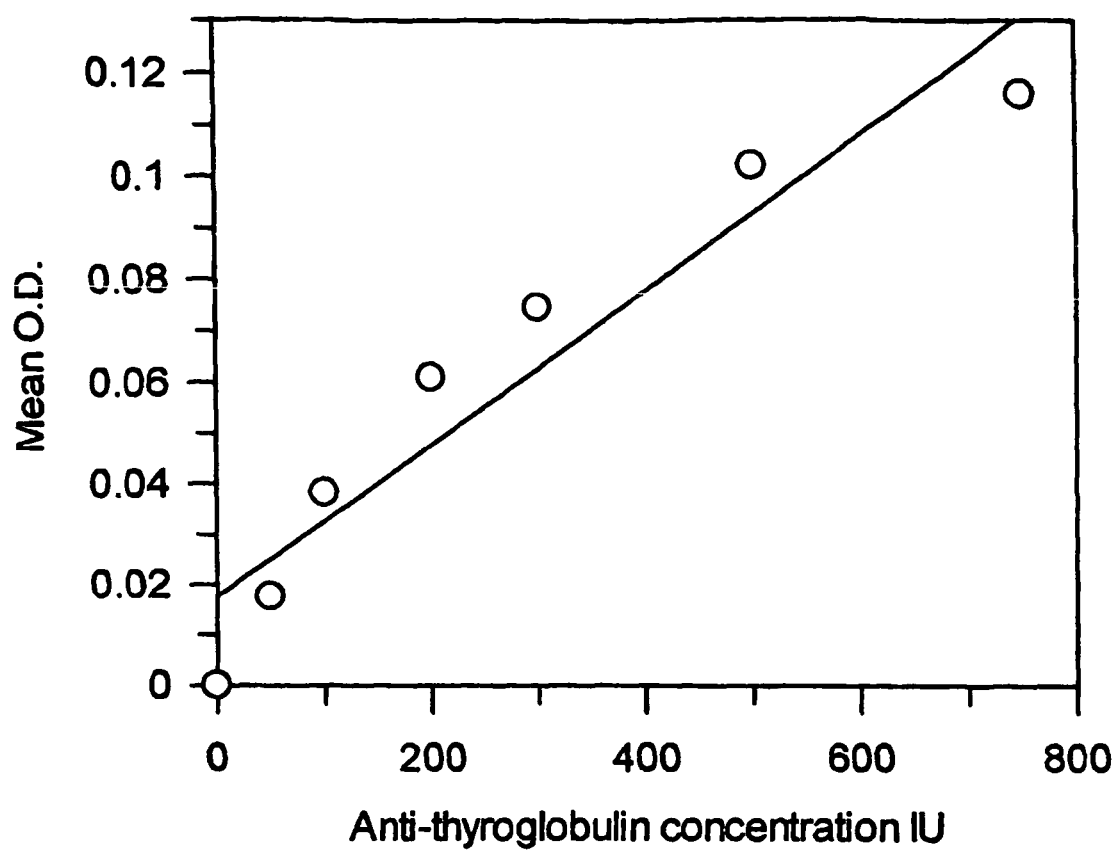

FIGS. 10 and 11—are anti-thyroglobulin calibration curves generated using MeDAB as HRP substrate. (correlation coefficient for FIG. 11 is 0.88).

Figure 12:
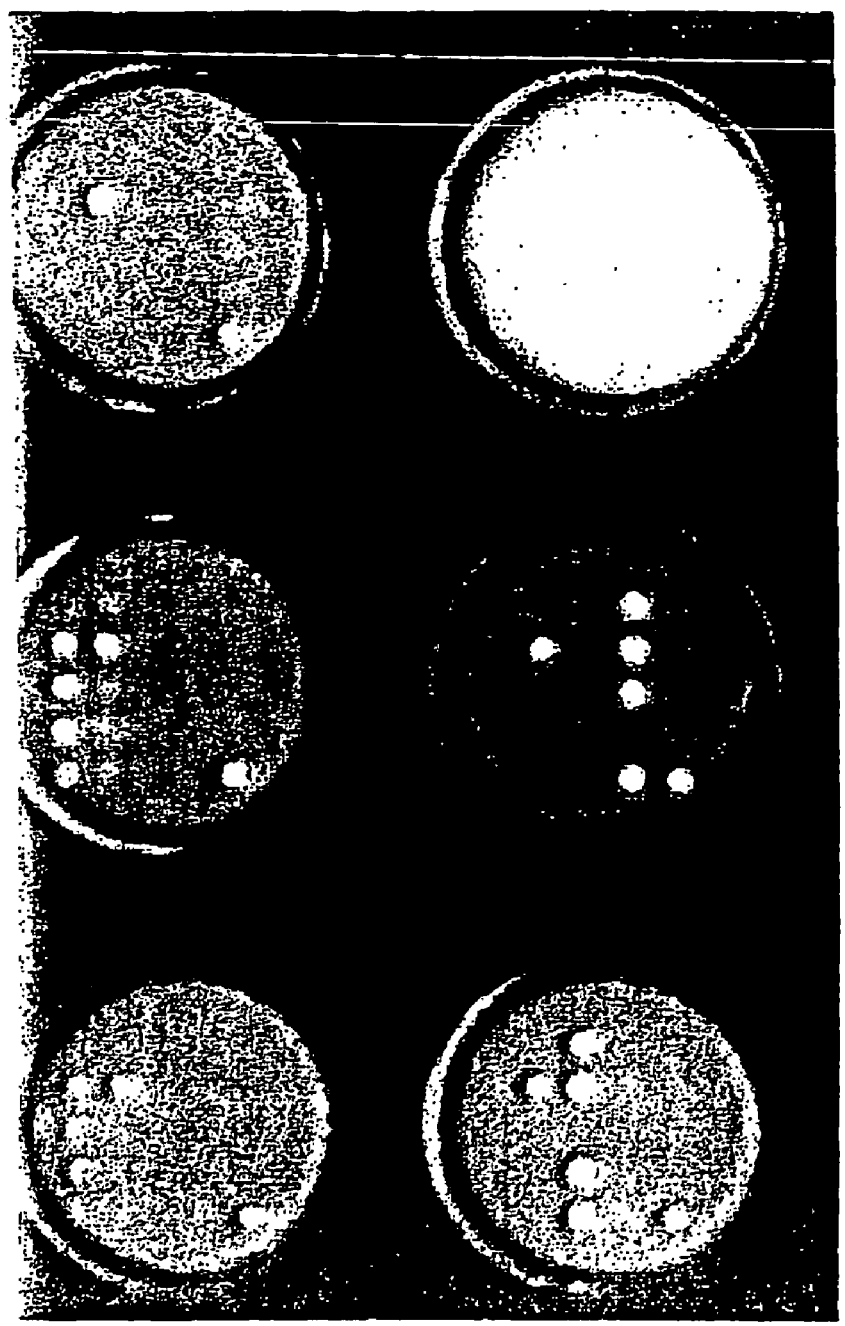
FIG. 12 shows the results of a filtration microarray assay in accordance with the present invention and Example 3.

FIG. 12—representative positive sera at 1/1000 dilution. Consistent bright spots in columns 2 and 5 are standard positive controls. Bottom left, anti-RNP/Sm positive sera—Sm column slightly (Col 2) +ve c.f. RNP/Sm (Col 1), bottom right, anti-Scl 70 positive serum, middle left, anti-Sm positive serum, middle right, anti-Jo1, upper left, anti Ro (SS-A) serum, upper right, all 5 anti-sera combined (compare Example 3).

Figure 13:
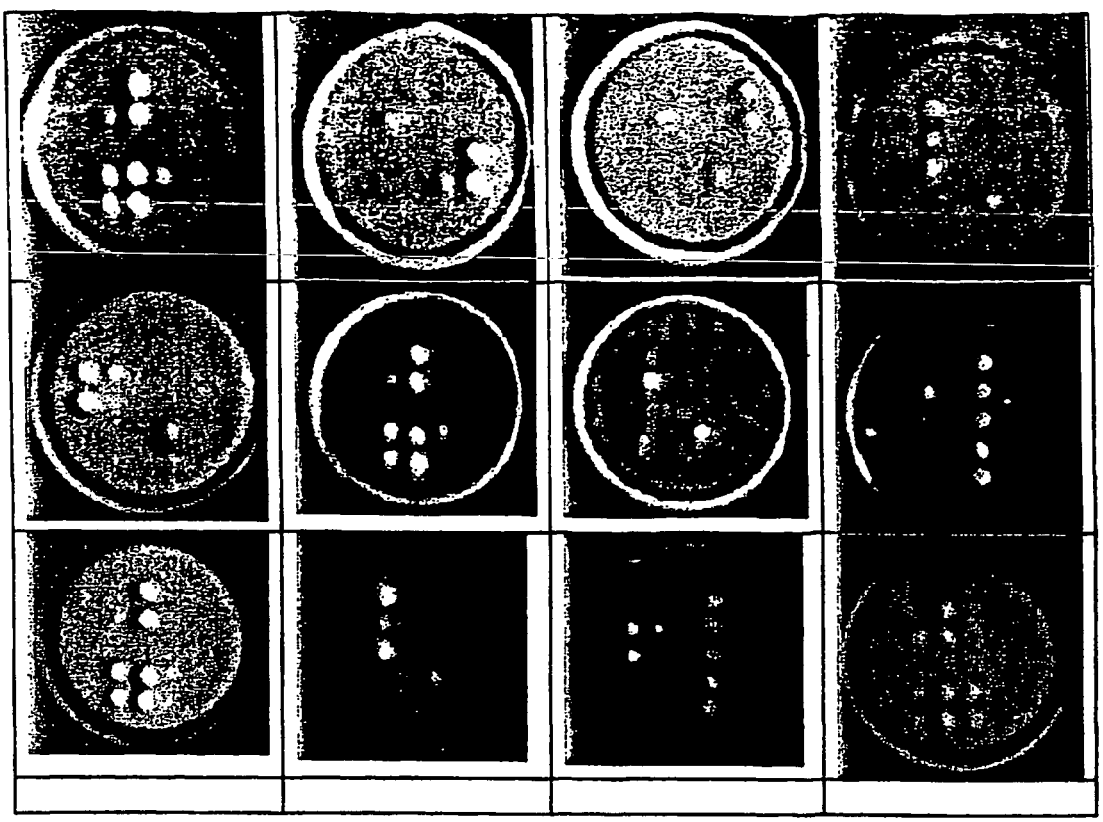
FIG. 13 shows the results of a filtration microarray assay in accordance with the present invention and Example 4.

FIG. 13—representative images of array-wells incubated with sera or standard solutions. Top row, from left to right, Anti-sm serum from the National Health Service (NHS) diluted 1/800, anti-scl 70 serum (NHS) diluted 1/800, anti Jo1 (NHS) diluted 1/800, and Hashimoto's patient serum diluted 1/400. Middle row, anti-La (SS-B) serum (NHS) diluted 1/400, anti Sm-RNP serum (NHS) diluted 1/800, incubation buffer (PBST), and patient serum displaying anti-Ro activity. Bottom row, patient serum diluted 1/400 displaying anti Sm with or without anti-RNP activity (RNP is only present as a probe in complex with Sm), 750 IU anti-thyroglobulin standard, patient serum diluted 1/400 showing anti-Ro (SS-A) and La (SS-B) activity, and patient serum displaying anti sm with or without anti-RNP activity (note that the Sm probe signal is less than that of the Sm-RNP probe complex signal).

Figure 14:
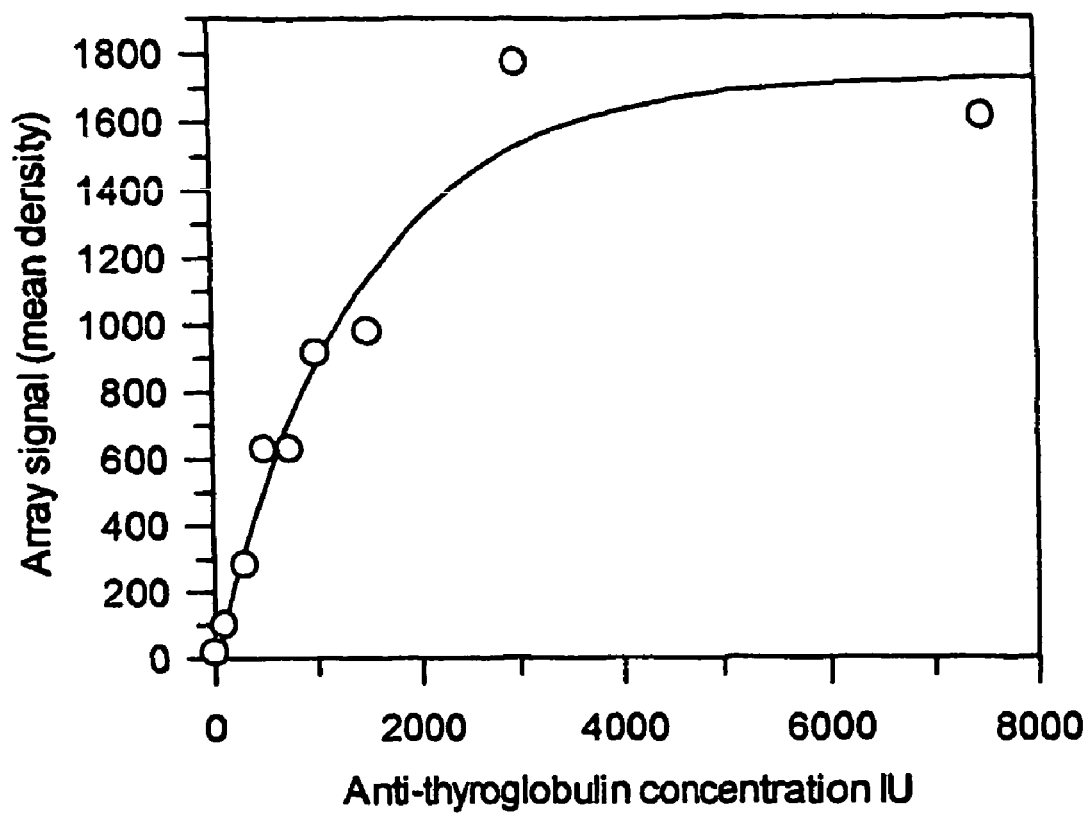
FIGS. 14 and 15 show calibration curves generated in accordance with Example 4.
Figure 15:
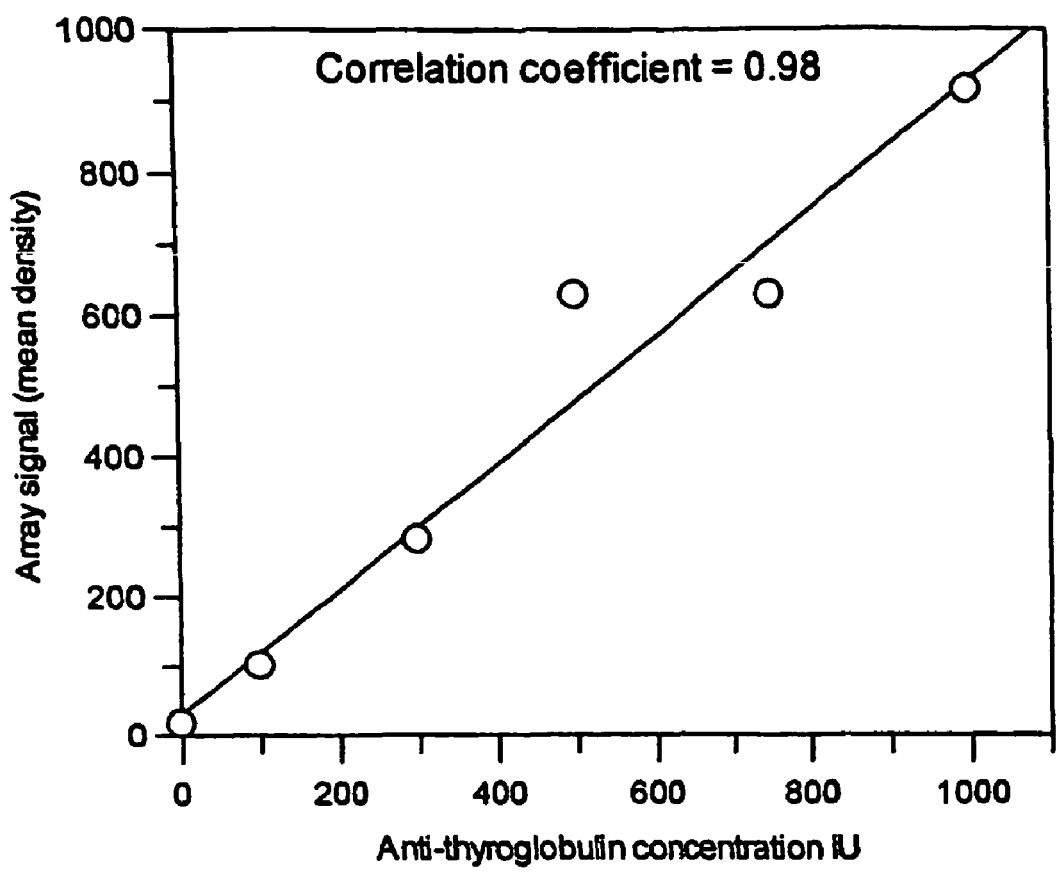

FIGS. 14 and 15—are calibration curves generated by incubation of standard anti-thyroglobulin solutions with immobilised thyroglobulin as capture probe, and performed in conjunction with a qualitative rheumatology auto-antigen array. Array signal is the mean density using a CCD exposure time of five seconds.

Figure 16:
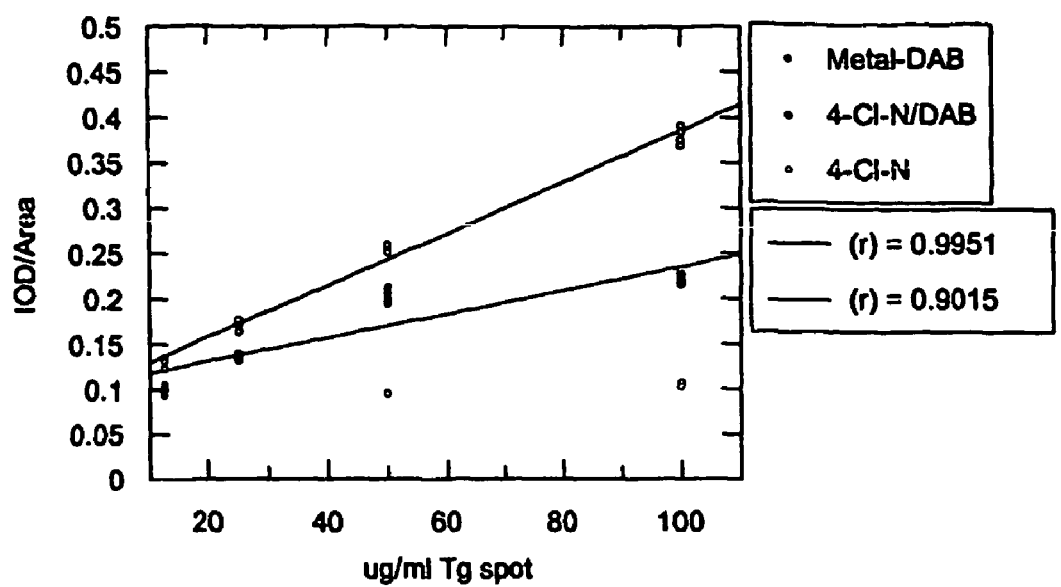
FIG. 16 is a graphic representation of probe sensitivity in a colourimetric nanodot assay.

FIG. 16—probe sensitivity of colourimetric nanodot assay. Assay performed with 1000 IU anti-Tg Std. and 1/1250 anti-human IgG+1/250 Strep-HRP as secondary cocktail. Flat bed scanner as detector.

DETAILED DESCRIPTION

Various preferred features and embodiments of the present invention will now be described by way of non-limiting examples and with reference to the accompanying drawings.

The present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The present invention relates to an apparatus for use in assays for detecting and/or quantifying the presence of one or more analytes in a sample and to methods of performing such assays.

Assays and Apparatus

In its simplest form, the apparatus of the present invention consists of a receptacle, the base of which consists of a porous membrane onto the underside of which is tethered (or "immobilised") a probe chosen for its ability to bind a target analyte. In use, a sample, in fluid form, is added to the receptacle and allowed to filter or pass through the membrane with or without positive or negative pressure applied from above or below the membrane to optimise binding kinetics. This, in turn, permits any analytes present in solution to bind to (or be bound by) the probe. Binding can then be detected and/or measured using standard methods (e.g. fluorescence labelling).

Embodiments of apparatus according to the present invention and useful in the method of the invention are shown in FIGS. 1A and B and FIG. 2.

In one embodiment of the present invention, as illustrated in FIG. 2, the probe(s) may be contained on the underside of a membrane of a first receptacle as an array of spots. The analyte solution may pass through the membrane and any second receptacle or be held at the second receptacle for interaction with the probe. In this case some of the analyte solution will also be above and also within the membrane. Cellular material is filtered by the membrane on the upper surface of the membrane, whilst the probe-analyte interaction predominates on the lower surface. Cellular and/or particulate matter is thus retarded from the lower surface thus reducing background when detection is performed by imaging means.

In more detail, in an embodiment of the present invention, microarrays comprising, for example 5×5 1-50 nl, or 5×5 12-20 nl, spots (which may be a mixture of probes and controls) may be printed upon the underside of a filter plate such as that shown in FIGS. 1A and B.

Upon drying and blocking of non-spotted surfaces, the under-filter area may be re-enclosed with a flexible underdrain containing a fluid trap to present sample solution to the array.

Samples are added within the wells from above (as with traditional ELISA type assays). The sample is allowed to pass through the membrane for example by gravity, positive displacement or partial vacuum. The approach taken may depend upon whether a continuous or step-wise filtration process is required. Probe/analyte interaction occurs as the sample is drawn past the probe spots or incubated in the fluid trap.

The membrane may be subsequently washed (preferably more than once) and co-incubated with a labelling agent (e.g. a labelled antibody). Again, reagents may be added to the well from above, allowing the porous membrane to act as a filter. The washing process may then repeated to remove any unbound label.

Figure 3:
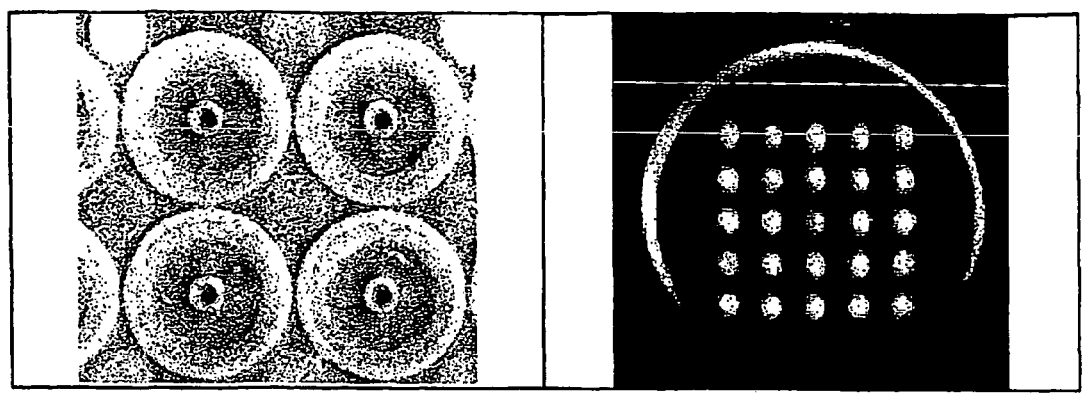
FIG. 3 shows (A) the under-well area detected by chemiluminescence and (B) a 5×5 20 nl array detected by a charge coupled device (CCD)

Finally, detection of spots showing interaction is achieved by detection methods known in the art (e.g. detection methods used for microarrays such as colourimetric and/or chemiluminescent reagents, and imaging techniques). Images obtained in this manner are shown by way of illustration in FIG. 3.

According to a preferred embodiment of the present invention, the apparatus comprises a plurality of receptacles (also referred to herein as "wells") forming a multi-well plate. The multi-well plate may be a 96-well (or microwell) plate, a 384-well plate or a 1536-well plate, allowing numerous samples to be analysed simultaneously (in e.g. high throughput screens). The plates will be of standard size and dimensions such that they can be used with existing robotics and automated systems. They are preferably formed of plastics materials such as polypropylene resin.

In more detail, 96-well plates of the present invention will preferably have a receptacle volume of approximately 0.4-0.5 mL. 384-well plates will preferably have a receptacle volume of approximately 10-100 µl with a standard 96-well footprint. 384-well plates are particularly suited to high volume DNA library manipulations and high throughput screening. 1536-well plates will preferably have a receptacle volume of approximately 1-15 µl, again with a standard 96-well footprint. 1536-well plates are particularly suited to automation and ultra high throughput screening.

The apparatus of the present invention is formed essentially from plastics materials including, but not limited to: polymethylmethacrylate, polystyrene, polyethylene, polypropylene and derivatives thereof. The material is chosen for its resistance to chemicals, solvents and alcohols. The plates may be clear when used for colourimetric reading, or coloured, e.g. white or black for luminescence and/or fluorescence reading.

As mentioned above, the base of each receptacle comprises a porous membrane. Preferably, the base will be flat-bottomed to maximise optical quality and imaging area.

Each receptacle comprises a fluid inlet and a fluid outlet. The fluid outlet comprises a porous membrane onto the underside of which at least one analyte-specific binding agent is tethered (this surface of the porous membrane is therefore also referred to as the "reaction zone"). The membrane will be permeable to the liquid portion of a sample and to the target analyte but impermeable to, and therefore capable of trapping, other (usually larger) components of the sample. It may be formed of a woven or non-woven fabric, paper, cellulose, glass fibre, polyester (or other polymer) or mixtures and derivatives thereof. Preferably, it will be formed of a mixed cellulose ester or nylon composition. Pore sizes will be in the range 0.01-1 µm, preferably in the range 0.1-0.5 µm, even more preferably in the range 0.4-0.5 µm. Ideally, the pore size will be about 0.45 µm. The membrane may be coated to create a hydrophobic surface, for example with poly-L-lysine, thereby improving stability and minimising spreading of the spots.

In one embodiment, one or more further porous membranes can be placed within each receptacle. Preferably, the membranes are positioned such that pore size gradually decreases from fluid inlet to fluid outlet. The pore sizes of the further membranes will vary depending on the sample to be filtered. Preferably, they will be in the range 0.01-10 µm, even more preferably in the range 0.1-5 µm, most preferably in the range 0.1-1.0 µm.

One or more of the membranes (including the final, reaction zone membrane) may comprise a "binder". The binder may be an antibody, ligand or other complementary molecule capable of binding unwanted cellular components or impurities, thereby improving the ability of these membranes to filter unwanted compounds from the sample. If a binder is included in the final membrane, it will preferably be positioned on the upper-side of said membrane (i.e. on the opposite surface to the reaction zone).

The apparatus of the invention may further comprise an "underdrain" or "collection tray" formed of one or more receptacles corresponding to the one or more wells of the apparatus such that, in use, each well is positioned at least in part in a corresponding receptacle. According to this embodiment, sample passing through the fluid outlet is collected in the receptacle allowing the membrane and any binding agents immobilised thereon to be bathed in the sample. This, in turn, increases interaction between the analyte and analyte-specific binding agent and therefore improves the sensitivity of the assay.

The apparatus may also comprise means for drawing liquid from the receptacle through the fluid outlet. Said means may consist of a vacuum pump, an air pressure pump, an adsorptive layer or any other standard means known in the art. Positive displacement can also be used for drawing liquid from the receptacle. Such means can be used to regulate the flow rate of the sample to achieve optimal reaction between the analyte and its binding partner.

Analytes and Analyte-Binding Agents

The term "analyte" as used herein refers to a compound or composition to be detected or measured in a sample. "Sample" refers to any desired material, usually of biological origin, to be tested for the presence of a target analyte. A sample may include, but is not limited to: blood or serum; saliva, sputum, tears, sweat or other secreted fluids; urine or faecal matter; biologically derived fluids such as cerebrospinal fluid, interstitial fluid, cellular extracts and the like; samples of environmental origin such as water or earth; food samples such as meat products, fruit and vegetables; test drugs etc.

As will be understood by the skilled person, the target analyte can be any specific substance or component that one is desirous of detecting and/or measuring in a chemical, physical, enzymatic or optical analysis. The analyte according to the present invention may be a polypeptide, polynucleotide or any other chemical compound or complex of chemical compounds.

In more detail, analytes that can be detected/quantified using the device or method of the present invention include, but are not limited to: antigens (such as antigens specific to bacterial, viral or protozoan organisms including, for example, Streptococcus, Hepatitis and HIV); antibodies (particularly those induced in response to infection, allergic reaction, or vaccination); hormones (such as human chorionic gonadotropin—hCG—used as a marker for pregnancy, oestrogen, progestin, testosterone or corticosteroids), proteins (such as circulating plasma proteins used as disease markers), nucleic acids (including circulating plasma nucleic acids, used as disease markers), and other physiological substances (for example, human growth factors, haemoglobin and cholesterol); a variety of enzymes (such as aspartate aminotransferase, lactate dehydrogenase, alkaline phosphatase and glutamate dehydrogenase); therapeutic compounds (such as steroids, antibiotics, tranquillisers and anticonvulsants); drugs (such as cocaine, heroin and marijuana); contaminants and environmental pollutants (such as pesticides, herbicides and aromatic hydrocarbons); vitamins; and any number of other natural or synthetic substances.

As will be appreciated by one skilled in the art, the number of natural and synthetic substances which can be detected by the assay devices and methods of the present invention is extensive, and includes, but is not limited to, the following groups of compounds: ACE inhibitors, alcohol deterrents (for example, disulfiram), anti-allergics, anti-anginals, anti-arthritics, anti-infectives (including but not limited to antibacterials, antibiotics, anti-fungals, anti-helminthics, anti-malarials and anti-viral agents), analgesics and analgesic combinations, local and systemic anesthetics, appetite suppressants, anti-oxidants, anxiolytics, anorexics, anti-arthritics, anti-asthmatic agents, anti-coagulants, anti-convulsants, anti-diabetic agents, anti-diarrheals, anti-emetics, anti-epileptics, anti-histamines, anti-inflammatory agents, anti-hypertensives, anti-migraines, anti-nauseants, anti-neoplastics, anti-oxidants, anti-parkinsonism drugs, anti-pruritics, anti-pyretics, anti-rheumatics, anti-spasmodics, anti-tussives, adrenergic receptor agonists and antagonists, cardiovascular preparations (including anti-arrhythmic agents, cardiotonics, cardiac depressants, calcium channel blockers and beta blockers), cholinergics and anti-cholinergics, contraceptives, diuretics, decongestants, growth stimulants, herbal preparations, hypnotics, immunizing agents, immunomodulators, immunosuppresives, muscle relaxants, neurologically-active agents including anti-anxiety preparations, antidepressants, anti-psychotics, psychostimulants, sedatives and tranquillisers, sore throat medicaments, sympathomimetics, vasodilators, vasoconstrictors, vitamins, xanthine derivatives, various combinations of these compounds, and the like.

Presence of the target analyte in a sample will be assessed by detecting binding of said analyte to an analyte-specific binding agent. The term "analyte-specific binding agent" (also referred to herein as "binding agent", "probe" or "binding partner") should interact with the analyte such that the presence of the analyte can be determined and/or measured, either directly or indirectly. Thus, the binding agent should show at least some specificity for the analyte of interest as opposed to other components of the sample under test. In one embodiment "binding agent" is used to describe a member of a binding pair which interact either chemically or physically to form a complex. Thus, an "analyte-specific binding agent" refers to an agent which, because of its three-dimensional structure, is capable of interacting specifically with the target analyte. An "immobilised" binding agent refers to a binding agent that is tethered, adsorbed, embedded or affixed, either permanently or semi-permanently, to the underside of the porous membrane of the present assay device. The binding agent will be immobilised in such a way that its affinity for the target analyte is not significantly altered.

The nature of the binding agent used in the present invention will depend on the nature of the analyte to be detected. Possible binding pairs include, but are not limited to: antibody and antigen; antibody and hapten; hormone and receptor; virus and cellular receptor; biotin and avidin; carbohydrate and lectin; effector and receptor molecules; enzyme and cofactor; enzyme and substrate; enzyme and inhibitor; complementary nucleotide sequences; biotin and streptavidin; biotin and avidin; protein and DNA; protein and RNA; DNA and RNA; and protein and protein. Wherein the binding agent is a nucleotide sequence, it will preferably be an EST (Expressed Sequence Tag). Binding agents for use according to the present invention will be prepared and immobilised using standard methods known in the art. Polynucleotide probes, for example, can be prepared by PCR amplification.

It should be noted that, while binding agents are generally described herein as the immobilised member of the analyte/analyte-specific binding agent pair, it is not intended that the reverse be excluded. It is indeed possible (and, in the case of DNA analysis, often preferred) that the analyte be bound and the probe added in solution. It is then the probe, rather than the analyte, which is labelled for detection and/or quantification. Thus, for example, to test for the presence of a gene A of known sequence, genomic fragments from one or more patients are immobilised on a substrate. Labelled primers, corresponding to the sequence of A, are then added in solution. Binding of a primer to any of the immobilised fragments will indicate the presence of gene A in that patient's DNA.

The analyte-specific assay device and method of the present invention can easily be adapted for detection of further or different analytes simply by replacing the binding partner immobilised in the reaction zone. In a preferred embodiment, the device can be adapted simply by removing a used membrane from the base of a well and replacing it with a fresh membrane. The fresh membrane may be pre-prepared with one or more binding agents having been immobilised thereon or, alternatively, the one or more binding agents can be tethered to the membrane after it has been affixed to the well.

In a preferred embodiment of the present invention, a plurality of different binding agents is immobilised on the porous membrane of the or each receptacle in the form of an array, allowing more than one analyte to be detected simultaneously.

Arrays and Microarrays

Because the binding agent of the present invention is tethered to the underside of the porous membrane, a large amount of background staining can be avoided. This in turn means that sensitivity and accuracy is improved, allowing each well to be used to test for more than one analyte compound. Thus, in a particularly preferred embodiment, each well comprises a plurality of different binding agents.

The plurality of binding agents are preferably arranged in the form of an array. An array is an orderly arrangement of polynucleotide or polypeptide probes. Each probe in an array is immobilised in a defined area known as a "spot". Spots can be deposited manually or using any one of many automated printing process known in the art. Once the spots have been deposited, the membrane will be dried and the non-spotted areas blocked (with BSA or PVA, for example).

Depending on the size of the spots in an array, it will be referred to as a "macroarray" or a "microarray". Macroarrays contain spot sizes of about 300 microns or larger and can easily be imaged using standard gel and blot scanners. The spot sizes in microarrays are typically less than 300 microns in diameter. Microarrays usually contain thousands of spots.

The area of each spot for use in the present invention can be of any size and shape. For example, squares, ellipsoids, rectangles, triangles, circles, or portions thereof, along with irregular geometric shapes, may be used.

In one embodiment, each spot will have a surface area of between about 1 cm$^2$ and 10$^{-10}$ cm$^2$. In some embodiments each spot will have a surface area of less than about 10$^{-1}$ cm$^2$, 10$^{-2}$ cm$^2$, 10$^{-3}$ cm$^2$, 10$^{-4}$ cm, 10$^{-5}$ cm$^2$, 10$^{-6}$ cm$^2$, 10$^{-7}$ cm$^2$, 10$^{-8}$ cm$^2$ or 10$^{-10}$ cm$^2$. In a preferred embodiment, these regions are between about 10×10 μm and 500×100 μm. It is an advantage of the invention that, by "spotting" the underside (rather than the inside) of the well, a greater reaction surface becomes available. This is because the inside wall of the well interferes with the deposition of the spots on the periphery of the well. Thus, a greater number of spots per well can be included. Each reaction zone may comprise from one to several hundred thousand spots. Preferably, each reaction zone will comprise an array of 1, 5, 10 or more spots. In an even more preferred embodiment, each reaction zone will comprise an array of 50, 100, 500 or more spots. In a most preferred embodiment, each reaction zone will comprise an array of 4×4, 5×5 or 6×6 spots.

Together with the array of polynucleotide or polypeptide probes deposited onto the porous membrane of each well, it is preferable to also include at least one control probe against which results can be measured. Alternatively, when the apparatus comprises a plurality of wells, one or more of the wells can be used as controls. The sample added to the well(s) will contain a known concentration of each sample to be tested. Levels of binding in the control well(s) can then be used as a standard against which results can be measured.

According to an alternative aspect of the present invention, there is provided a multi-well plate (as defined above) wherein each well comprises an array of probes. The probes may be polynucleotide or polypeptide probes and may be tethered to the inside or to the outside of the well. If tethered to the inside of the well, the probes will preferably be positioned at its base. The base may be integrally formed with the rest of the well or it may be formed of a porous material for use in a filtration type assay. Preferably, the probes will be immobilised onto the underside of a porous membrane positioned at the base of the well (as described above).

In a preferred embodiment, the method of the present invention further includes a "washing" step comprising adding an aqueous solution to the or each well after the analyte/probe binding step in order to remove any unwanted matter (such as particulate or coloured material introduced by or with the sample solution, cellular components, etc.) from the reaction zone and to reduce any non-specific binding. A further washing step is preferably included after labelling to remove any unbound reagents and, again, to reduce any non-specific binding. Each washing step may include one or more (preferably a 4-6) washes. Inclusion of this step further improves the sensitivity and reliability of the present assay. In the present invention washing is greatly facilitated relative to conventional methods of aspiration by the filtration process.

Binding of the target analyte to an immobilised probe (or, conversely, binding of a probe to the immobilised target analyte) can be detected using any standard method known in the art.

Detection Methods

The assay methods of the present invention comprise a plurality of continuous or discontinuous steps. They can be described, in simple terms (and in accordance with certain preferred embodiments), as follows:

(a) providing an apparatus in accordance with the invention (e.g. a multi-well plate wherein each well comprises a porous membrane onto the underside of which is immobilised an array of probes);

(b) adding a sample to each well and allowing it to filter through the porous membrane such that analyte/probe binding occurs;

(c) optionally washing the membrane several times with an aqueous solution;

(d) adding labelling reagents to each well and allowing them to filter through the porous membrane such that analyte/label binding occurs (note: this step may be performed simultaneously with step b);

(e) optionally washing the membrane several times with an aqueous solution;

(f) detecting analyte/probe interaction and/or imaging.

Typical detection assays will use either a "competition" assay or a "sandwich" assay to detect/quantify binding of the target analyte. In a competition assay, the target analyte competes with a labelled analyte (or labelled analogue to the analyte) for an immobilized binding partner. A greater concentration of analyte in the sample results in a lower signal in the assay, as the labelled analytes are prevented from interacting with the immobilised binding partner. Thus, the signal produced during a competition assay decreases as the concentration of analyte in the sample increases.

In a sandwich assay, the target analyte is bound, or "sandwiched", between an immobilised, unlabelled first binding partner and a labelled second binding partner. Various further staining methods have evolved from this first and very simple method. For example, in the two-step indirect method, the target analyte is bound between two binding partners, one of which is immobilised. A labelled antibody, directed against the non-immobilised binding partner is then applied. This method is more sensitive than the direct method insofar as the labelled antibody is likely to react with a number of different epitopes on the non-immobilised binding partner, thus amplifying the signal and has greater specificity since more than one epitope on the analyte must be detected.

Further forms of detection will be apparent to the skilled person (e.g. from standard ELISA and DNA microarray assays). Further staining methods are described, for example, in the Handbook of Immunochemical Staining Methods, 3$^{rd}$ Edition (Thomas Boenisch, 2001, DAKO Corporation, California—see, in particular, pages 26-31), available at http://www.dakousa.com/ihcbook/hbcontent.htm.

The term "label" as used herein refers to any substance that is capable of producing a detectable signal. Labelling will be performed according to standard methods. Labels suitable for use in the present invention include, but are not limited to: chromatogens, fluorescent, chemiluminescent or bioluminescent compounds, radioisotopes or radionucleotides, catalysts, enzymes, enzyme substrates, cofactors, inhibitors or subunits, dyes, colloidal metallic and non-metallic particles, and organic polymer latex particles. Examples of specific labels include fluorescein, rhodamine, Texas red, phycoerythrin, umbelliferone, luminol, NADPH, α-β-galactosidase, horseradish peroxidase, etc.

Labels of use in the present invention can be divided into two types: those that can be detected by visual inspection (e.g. moieties which include or produce coloured elements such as colloidal metals, non-metals, and dye particles), and those which can only be detected with the aid of artificial detection systems (such as, for example, optical systems, spectroscopic systems and radiographic systems). Thus, according to a further embodiment of the present invention, the apparatus comprises means for detecting binding of an analyte to the analyte-specific binding agent.

The detecting means used will depend upon the nature of the label used. For example, if the label is a fluorescent label, the detecting means will be a fluorimeter. A large number of different fluorimeters are available in the art, any of which would be suitable for use in the present invention. With enzymes, either a fluorescent or a coloured product can be provided and determined fluorimetrically, spectrophotometrically or visually.

Preferably, the detecting means will be fluorimetric, chemiluminescent, radiochemical or colourimetric means. According to one embodiment, said means will be a photometric device capable of detecting and/or quantifying light emitted from the porous membrane such as a luminometer.

The detecting means may also or alternatively comprise imaging means capable of individually detecting and/or quantifying light emitted from each area of binding on the porous membrane (e.g. from each spot in an array). Possible imaging means include CCD (charge coupled device) apparatus and scanners. By placing the reaction zone on the underside of the apparatus, the present invention facilitates label detection and reading, thus allowing for more compact detection and/or imaging means to be used. Preferably, the detecting and/or imaging means will be formed integrally with the rest of the apparatus. Preferably, the detecting and/or imaging means will comprise a plurality of lenses, each lens corresponding to a well so that automatic reading of results can be performed.

Moving the reaction zone to the underside of the apparatus also means that interference caused by light reflecting off the receptacle walls is avoided and that levels of background interference from particulate matter can be reduced. Furthermore, a greater reaction surface is made available making it possible to include a greater number of spots in each array. This, in turn, means that the cost and time required for testing large numbers of analytes can be substantially reduced. The apparatus and methods of the present invention are therefore particularly suited to large scale genetic and proteomic studies and to ultra-high throughput screening.

Applications and Uses

The methods and devices according to the present invention can be used for both quantitative and qualitative assays. The most common applications of such methods will be for the determination of gene expression patterns (e.g. differential gene expression between identical cells subjected to different stimuli or between different cellular phenotypes or developmental stages), for immuno- and disease diagnostics and for studying protein function.

Such applications can be used, in particular, to gain a better understanding of disease pathology, i.e. what triggers the expression of a disease gene, its effect on the expression of other genes and on its host organism as a whole, its expression patterns across different populations, etc. This, in turn, will allow for diseases to be more easily diagnosed and treated. Many disease states are indeed characterised by differences in the expression levels of various genes either through changes in the copy number of the genetic DNA or through changes in levels of transcription of particular genes. Thus, changes in the expression levels of particular genes serve as signposts for the presence and progression of various disorders.

For example, the expression (or over-expression) of oncogenes can be an indicator for the onset of certain types of cancer, the detection of a specific genetic mutation can help to diagnose cystic fibrosis, etc. Similarly, viral infection is often characterised by the elevated expression of genes of the particular virus. Outbreaks of Herpes simplex virus, Epstein-Barr virus, cytomegalovirus, Varicella zoster virus, parvovirus and human papillomavirus, for example, are all characterised by elevated expression of various components of the respective viral genome. Thus, detection of elevated expression levels of characteristic viral genes provides an effective diagnostic of the disease state.

Expression levels can also be used to analyse the role of any given gene in the cell division cycle, development (cellular, embryonic, etc.), tissue differentiation and so on. Changes in levels of expression can be measured either in terms of mRNA transcription levels or in terms of protein levels. Thus, both the polynucleotide and polypeptide assays of the present invention can be used to study expression patterns and in diagnostic tests. The polypeptide assays can also be used to study protein interactions and, therefore, protein function.

Expression patterns are indeed insufficient to give a full picture of cellular and developmental mechanisms. While they may reveal which genes are involved in a particular process, it is also important to determine how they are implicated. Many proteins, for example, are involved in signalling pathways. These complex pathways provide a link between, for instance, the binding of a compound to a cell surface ligand and the downstream expression of a target gene. The present invention can be used, in this regard, to determine possible binding partners for any protein of interest (be they polypeptides, polynucleotides or any other type of chemical compound). For example, the assay of the present invention could be used to identify all compounds capable of interacting with the extracellular portion of a cell surface protein, which proteins are capable of binding a target DNA sequence, etc. Thus, the present invention can be used to provide a powerful insight into the exact function of any protein of interest and, on a larger scale, into the working of cellular mechanisms. It is a particular advantage of the present invention that many hundreds or thousands of compounds can be tested simultaneously, thereby substantially increasing the rate at which binding partners can be analysed.

Outside research and disease diagnosis, the present assay devices and methods can be used to detect and quantify toxins or other desirable or undesirable compounds in environmental and/or food samples. For example, they could be used to identify chemical compounds in a river which is suspected of being contaminated, for large scale drug screening, for determining levels of a given vitamin in a new food product and so on.

EXAMPLES

Materials

Reagents were obtained from the following sources:

PBS: 0.01 M phosphate buffer, 0.0027 M potassium chloride and 0.137 M sodium chloride, pH 7.4

PBST: 0.01 M phosphate buffer, 0.0027 M potassium chloride and 0.137 M sodium chloride, pH 7.4, 0.05% v/v Tween-20

Human thyroglobulin was from Calbiochem (San Diego, Calif., USA)

Standardised anti-thyroglobulin solutions were provided by Cambridge Life Sciences (Cambridgeshire, U.K.).

Extractable nuclear antigens; proteinaceous La (SS-B), ribonucleoproteins-Smith complex (RNP/Sm), topoisomerase (Scl 70) and proteinaceous Ro (SS-A) from calf thymus and histidyl sRNA synthetase (Jo1) and the polypeptide Smith (Sm) and from bovine thymus are products of AroTec Diagnostics Ltd, New Zealand but were supplied by The Binding Site, Birmingham, U.K.

Reference, pooled human serum previously tested and shown to display anti-Sm, anti-Sm & RNP, anti-Jo1 & Scl 70, anti-Ro & La, anti-Jo1, or anti-Scl 70 activities from the National Health Service (NHS; UK) and Anti-human thyroglobulin were supplied by Cambridge Life Sciences, Cambridge, U.K.

Biotinylated Bovine serum albumin (Biotin-BSA) was a product of Vector Laboratories U.K., Peterborough, U.K.

Biotinylated goat polyclonal to human IgG H&L from Abcam, Cambridge, U.K.

Streptavidin-Horseradish peroxidase (HRP) polymer from Sigma (Poole, U.K).

Super Femto ELISA, 4-Chloro-1-napthol+3,3'-Diamino benzamidine (4Cl—N/DAB) and metal enhanced 3,3'-Diamino benzamidine (MeDAB), were products of Pierce (Rockford, Ill., U.S.A.).

Mixed cellulose ester membrane bottomed 96 well plates (Multiscreen) with a porosity of 0.45 μm, and a flexible, removable under-drain were a product of Millipore (Millipore, U.K. Watford, Millipore, U.K.).

Array Fabrication Prior to Bioassay.

Antigens were diluted in 50 mM Bicarbonate pH 9.5, 0.005% Bromophenol blue and 2.5% v/v glycerol to concentrations between 10-200 μg/ml and transferred into 96 well plates (precise concentrations given in the examples below). A robotic microarrayer, BioDot AD3200, with microsolenoid inkjet valve and ceramic tip (100 μm for 12 nl and 190 μm for 20 nl probe spots) was employed for non contact printing of spot-arrays (Bio-Dot, Cambridge, UK) onto the under-well surface of mixed cellulose ester microplates (the under-drain was first removed) in an ordered array as described in the examples (using the AxSys software supplied by the manufacturer). The spotted arrays were kept in a moist chamber at 4° C. overnight. Thereafter, inside the wells were washed 3×200 μl with PBS, 'flicking' out each time, followed by 3×100 μl on the under-surface. The under-drain was replaced, and the membrane blocked by the addition of 0.8% PVA in 0.1M phosphate buffer pH 7.2, shaking for one hour on a reciprocal shaker (Eppendorf 5436 thermomixer, Eppendorf, U.K.) before washing the plate using a vacuum (~200 ul/well/30 secs) 3×200 μl PBST. Thereafter, the plates were ready for bioassay or alternatively allowed to air dry for storage at 4° C.

Example 1

Estimation of Anti-Thyroglobulin Concentration Using Chemiluminescent Detection (FIGS. 4-6)

(A) 20 nl of 10 μg/ml thyroglobulin was spotted as a 5×5 array per well.
(B) 100 μl standardised anti-Thyroglobulin solutions in PBST were pipetted into individual wells, and stood at room temperature on an empty reagent reservoir/tray for 60 minutes.
(C) Washing was performed by evacuating wells using a vacuum manifold designed for the plates (Millipore, U.K.) and a mechanical vacuum source to give an evacuation rate of ~200 μl/well/30 seconds. The process was repeated three further times after the addition, each time of 200 μl PBST.
(D) 100 μl of a mixture giving 1/5000 goat polyclonal to human IgG H&L and 1/2000 streptavidin-HRP polymer was freshly prepared in PBST and pipetted within the wells, again, incubation was performed by standing at room temperature for 60 minutes upon an empty reagent reservoir/tray.
(E) Washing was repeated as step C, followed by two additional steps with 200 μl deionised water. The under-drain was removed, and the plate placed upon an empty reagent reservoir/tray.
(F) 100 μl of HRP substrate (Super Femto ELISA, Pierce) prepared as described by the manufacturer was added to wells, and allowed to pass through the membrane. After 150 seconds, the lower surface was blotted using tissue. Probe-analyte interaction was detected as regions of enzyme-linked HRP activity yielding a chemiluminescent signal.
(G) Images for analyses were acquired using a Charge Coupled Device-based Fast Digital Imager camera (hereafter referred to as CCD), manufactured by Photonic Science Ltd (Robertsbridge, U.K.) housed inside a custom-built light-tight chamber. The camera was positioned underneath the microplate and focussed at the plane of the membranes. A 6-second exposure time was used for capturing the images. The camera was controlled by drivers incorporated into the Image-Pro Plus version 4.0 (Media Cybernetics Inc., MD, USA) data analysis package. Images were saved as 12-bit grey scale TIFF files. Thermal build-up in the CCD during each exposure was removed by subtracting a dark image of the same exposure time. This process added a bias of ~100 counts to each pixel of data, to prevent negative numbers being generated in pixels with low signal. Prior to evaluation, each image was then flat-fielded to remove the effects of lens vignetting and any artefacts in the optical chain. The flat-field data used within this procedure was obtained by acquiring images of 3 separate areas of a special, uniformly illuminated, screen and averaging the three images to remove any small-scale variations. A representative image is shown in FIG. 4.
(H) ArrayPro 4.0 software (Media Cybernetics Inc.) was used to determine the mean intensities of feature and background pixels. Intensity levels represent the mean density values from 25 identical thyroglobulin probe features within a sampling area of 3 pixels diameter. Local, within-well, background pixel intensity was subtracted from spot signals using the 'local corner' function within ArrayPro. Calibration curves were fitted to the data using linear and non linear regression analysis with GraFit 5.0 software (Erithacus software, Staines, UK) and are shown as FIGS. 5 and 6.

Example 2

Colourimetric Assay of Anti-Thyroglobulin Concentration (FIGS. 7-11)

(A) 20 nl of thyroglobulin was spotted as a 5×5 array per well, with 5 spot columns comprising 100, 50, 25, 12.5 and zero μg/ml concentration (shown as rows in FIG. 7).
(B) After fabrication, 50 μl standardised Anti-Thyroglobulin solution or patient serum in PBST was added into individual wells, the plate was placed on an empty reagent reservoir/tray and shaken for 60 minutes at room temperature, 500 rpm on a reciprocating shaker (Eppendorf 5436 thermomixer, Eppendorf, U.K).
(C) Washing was performed by evacuating wells using a vacuum manifold designed for the plates (Multiscreen vacuum manifold, Watford, Millipore, U.K.) and mechanical vacuum source to give an evacuation rate of ~150

μl/well/30 seconds. The process was repeated three further times after the addition, each time of 150 μl PBST.

(D) 100 μl of a mixture giving 1/1250 goat polyclonal to human IgG H&L and 1/250 streptavidin-HRP polymer was freshly prepared in PBST and pipetted within individual wells, the plate was again placed on an empty reagent reservoir/tray and shaken at 500 rpm, room temperature for 60 minutes.

(E) Washing was repeated as step C, twice with PBST, twice with deionised water. The under-drain was removed, and the plate suspended on an empty reagent reservoir/tray.

(F) 100 μl of HRP substrate, either 4-Chloro-1-napthol+3,3'-Diamino benzamidine or Metal enhanced DAB (Pierce) prepared as described by the manufacturer was added to individual wells and allowed to pass through the membrane whilst shaking at ~500 rpm for between 5 to 60 minutes. Probe-analyte interaction was detected as areas of precipitated, coloured product by the enzyme-linked HRP activity.

(G) The under-well surface images for analysis were acquired using a conventional flat bed scanner (Agfa SnapScan 1212u and operating software, Scanwise v2.0) and saved as 16-bit grey scale TIFF images. To show the effect of filtration of the sample and/or substrate, the upper surface (within well) of the membrane was also scanned (FIG. 7).

(H) The saved under-well images were analysed in terms of Optical Density using ArrayPro. Calibration of an image was performed within this software by defining black (the scanner lid) and incident levels (a blank area of membrane) using a 3×3 pixel sample area of the image. Optical density values represent the mean of 5 identical thyroglobulin probe features (using those spotted at 100 μg/ml) for a given well-membrane. These values were corrected for local background by subtracting the mean of 5 identical buffer spots (in place of probe antigen) upon the same well-membrane. Calibration curves were again performed using the GraFit 5.0 software. These curves are shown as graphs in FIGS. 8-11.

Example 3

Rheumatology Autoantigen Array Employing Chemiluminescent Detection (FIG. 12)

(A) 20 nl of 10 μg/ml Antigen or control was spotted in the following array-order per well:

|   | 1 | 2 | 3 | 4 | 5 |
|---|---|---|---|---|---|
| 1 | −ve | Sm | Scl 70 | Jo 1 | Ro(SS-A) |
| 2 | RNP/Sm | +ve | Scl 70 | Jo 1 | Ro(SS-A) |
| 3 | RNP/Sm | Sm | −ve | Jo 1 | Ro(SS-A) |
| 4 | RNP/Sm | Sm | Scl 70 | −ve | Ro(SS-A) |
| 5 | RNP/Sm | Sm | Scl 70 | Jo 1 | +ve |

Where −ve = negative control, spotting buffer, +ve = positive control 1 μg/ml Biotin-BSA.

(B) 100 μl pooled NHS reference serum at 1/1000 dilution, patient sera or buffer was added to individual wells. The plate was placed upon an empty reagent reservoir/tray, incubated with shaking (500 rpm) for 60 minutes, room temperature.

(C) The plate was then washed 3× with 200 μl PBST wash using the Millipore vacuum apparatus at a flow rate of approximately 200 μl/well/thirty seconds.

(D) Secondary incubation was performed with a cocktail of freshly prepared 1/10,000 anti-IgG (Biotin), 1/2000 Streptavidin-HRP in PBST. Again the plate was placed upon an empty reagent reservoir/tray, incubated with shaking at 500 rpm for 60 minutes at room temperature.

(E) Washing was then repeated using the vacuum apparatus, but with 2×200 μl PBST followed by 2×200 μl PBS wash steps. The under-drain was removed, and the plate placed upon an empty reagent reservoir/tray.

(F) HRP substrate (Super Femto ELISA, Pierce) was prepared as described by the manufacturer and 100 μl was added to individual well, allowed to pass through the membrane for 2.5 minutes before gently blotting the under-surface three times with tissue paper. Image analysis employed the CCD-FDI camera (Photonic Sciences) controlled by the Image-Pro Plus software. Probe-analyte interaction was detected as regions of enzyme-linked HRP activity yielding a chemiluminescent signal.

Example 4

Qualitative Rheumatology Autoantigen Array Combined with a Quantitative Thyroglobulin Autoantigen Assay Employing Chemiluminescent Detection (FIGS. 13-15)

Rheumatology Array

Antibodies to Ro and La are often found in systemic lupus erythematosus (SLE) and Sjogren's syndrome (SS) patients. Anti-Ro antibodies in the mother are also strongly associated with congenital heart block. Anti-Sm antibodies are present in approximately 30% of patients with SLE and are widely regarded as a disease marker. Where a sample shows a negative Sm result, anti-RNP antibodies are present in 90% of mixed connective tissue disease (MCTD) patients. Anti-Jo-1 antibodies are classically found in patients with scleroderma.

Thyroglobulin Assay

Autoimmune thyroid gland disorders are characterised by the detection of anti-thyroid antibodies including thyroglobulin (Tg) and thyroid peroxidase (TPO). Both of these thyroid components play key roles in the biosynthesis of thyroid hormones. Circulating autoantibodies to Tg and TPO are present in up to 90% of patients with thyroiditis, idiopathic hypothyroidism, Graves' disease and subacute thyroiditis. Of all the autoimmune conditions, Graves' disease and Hashimoto's thyroiditis are perhaps the easiest to treat, provided that they are detected at an early stage. This requires sensitive detection of antibodies to Tg (and TPO), together with the ability to monitor the antibody response to drugs, radiotherapy or surgery.

(A) A 5×5 array of 12 nl spots was generated using 15 μg/ml antigen (Sm at 30 μg/ml) or 2 μg/ml Biotin-BSA as positive control and spotting buffer as negative control. Array Scheme:

|   | 1 | 2 | 3 | 4 | 5 |
|---|---|---|---|---|---|
| 1 | −ve cont | Tg | Sm/RNP | Ro(SS-A) | Jo-1 |
| 2 | La(SS-B) | +ve cont | Sm/RNP | Ro(SS-A) | Jo-1 |
| 3 | La(SS-B) | Tg | −ve cont | Ro(SS-A) | Scl 70 |
| 4 | BSA | Sm | Sm/RNP | +ve cont | Scl 70 |
| 5 | BSA | Sm | Sm/RNP | Ro(SS-A) | −ve cont |

(B) The plate was placed upon an empty reagent reservoir/tray, 100 μl pooled NHS reference serum, anti-thyroglobulin standard solutions or patient sera in PBST were pipetted into individual wells and shaken for 60 minutes at room temperature (500 rpm)

(C) Washing was performed with the Millipore vacuum apparatus, 3× with 200 µl PBST.

(D) The plate was again placed upon an empty reagent reservoir/tray, 100 µl of a freshly prepared mixture comprising 1/10,000 anti-IgG (Biotin) and 1/2000 Streptavidin-HRP in PBST was pipetted into individual wells for 60 minutes, at room temperature and shaken at 500 rpm.

(E) The vacuum washing step was repeated, with 2×200 µl PBST, 2×200 µl deionised water. The under-drain was removed, and the plate placed upon an empty reagent reservoir/tray.

(F) HRP substrate (Super Femto ELISA, Pierce) was prepared as described by the manufacturer and 100 µl was added to individual well, allowed to pass through the membrane for 2.5 minutes before gently blotting the undersurface three times with tissue paper. Probe-analyte interaction was detected as regions of enzyme-linked HRP activity yielding a chemiluminescent signal. Image analysis employed the CCD (Photonic Sciences) controlled by the Image-Pro Plus software.

(G) Images for analysis were acquired and analysed as example 1, except exposure times ranged from 2 to 10 seconds, and localised, within well background was subtracted from feature spots using the signals of negative control spots (spotting buffer).

(H) Calibration curves for thyroglobulin features were then constructed as previously, but using a five second exposure times. Intensity levels represent the mean density values from duplicate thyroglobulin features within a sampling area of ~3 pixel diameter.

(I) In all cases, the activity of reference sera was confirmed as was patient sera previously tested by the local diagnostic clinic. Relative probe signals in patient sera could be inferred by sera titration and/or by the signal resulting from alteration of CCD exposure times.

(J) Quantitative anti-thyroglobulin levels in patient serum displayed similar results to those employing conventional ELISA (not shown).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

The invention claimed is:

1. An apparatus for use in an assay comprising:
   (a) at least one first receptacle comprising a fluid inlet and a fluid outlet;
   (b) a porous membrane; and
   (c) at least one analyte-specific binding agent,
   characterized in that said at least one analyte-specific binding agent is immobilised on the underside of said porous membrane relative to the fluid inlet wherein the porous membrane is positioned at the fluid outlet.

2. An apparatus according to claim 1, wherein said at least one first receptacle comprises a plurality of said first receptacles in the form of a multi-well plate.

3. An apparatus according to claim 1, wherein a plurality of analyte-specific binding agents is immobilised on said porous membrane in the form of an array.

4. An apparatus according to claim 3, wherein the array comprises at least one control probe.

5. An apparatus according to claim 1, further comprising a means for drawing liquid from the at least one first receptacle through the fluid outlet.

6. An apparatus according to claim 1, further comprising a means for drawing liquid from the at least one first receptacle through the fluid outlet and wherein the drawing means is a vacuum pump.

7. An apparatus according to claim 1, further comprising a means for detecting binding of an analyte to the binding agent.

8. An apparatus according to claim 1, further comprising a means for detecting binding of an analyte to the biding agent and wherein the detecting means is selected from fluorimetric, chemiluminescent, radiochemical, physical and colourimetric means.

9. An apparatus according to claim 1, further comprising a means for detecting binding of an analyte to the binding agent and wherein the detecting means comprises a photometric device capable of detecting and/or quantifying light emitted from porous membrane (b).

10. An apparatus according to claim 1, further comprising a means for detecting binding of an analyte to the binding agent and wherein the detecting means comprises a photometric device and the photometric device is a luminometer.

11. An apparatus according to claim 1, further comprising a means for detecting binding of an analyte to the binding agent and wherein the detecting means comprises imaging means.

12. An apparatus according to claim 1, wherein said at least one analyte-specific binding agent is a polynucleotide probe.

13. An apparatus according to claim 1, wherein said at least one analyte-specific binding agent is an Expressed Sequence Tag (EST).

14. An apparatus according to claim 1, wherein said at least one analyte-specific binding agent is a polypeptide binding agent.

15. An apparatus according to claim 1, wherein said at least one analyte-specific binding agent is an antibody or a fragment thereof.

16. An apparatus according to claim 1, wherein said at least one analyte-specific binding agent is immobilised directly or indirectly on said porous membrane.

17. An apparatus according to claim 1, wherein the or each first receptacle is positioned at least in part in a second receptacle which is capable of collecting liquid from the fluid outlet of the first receptacle such its porous membrane may be submerged in said liquid.

18. A method of detecting an analyte comprising:
   (a) providing an apparatus according to claim 1;
   (b) loading a sample to be tested into the or at least one of the first receptacles; and
   (c) detecting binding of the analyte to the analyte-specific binding agent.

19. A method of detecting an analyte comprising:
   (a) providing an apparatus comprising at least one first receptacle having a fluid inlet and a fluid outlet and having a porous membrane;
   (b) immobilising a plurality of analyte-specific binding agents in an array on the underside of said porous membrane;
   (c) loading a sample to be tested into the at least one first receptacle; and
   (d) detecting binding of the analyte to the analyte-specific binding agent(s).

20. A method according to claim 19 wherein the sample comprises a detectable label.

21. A method according to claim 20 wherein the detectable label is selected from an enzyme, a fluorescent label and a radiolabel.

22. A method according to claim 19 wherein step (d) comprises detecting binding of the analyte to the analyte-specific binding agent using any one of fluorimetric, chemiluminescent, radiochemical, physical and colourimetric means.

23. An apparatus for use in an assay comprising:
(a) at least one first receptacle comprising a fluid inlet and a fluid outlet;
(b) multiple porous membranes positioned between said fluid inlet and said fluid outlet, each porous membrane having a pore size; and
(c) at least one analyte-specific binding agent,
characterized in that said at least one analyte-specific binding agent is immobilised on the underside of one of said porous membranes relative to the fluid inlet, wherein the porous membranes are positioned within said at least one first receptacle so that the pore size of the porous membrane nearer the fluid inlet is greater than the pore size of the porous membrane nearer the fluid outlet.

24. An apparatus according to claim 23, further comprising a means for drawing liquid from the at least one first receptacle through the fluid outlet.

25. An apparatus according to claim 23, further comprising a means for drawing liquid from the at least one first receptacle through the fluid outlet and wherein the drawing means is a vacuum pump.

26. An apparatus according to claim 23, further comprising a means for detecting binding of an analyte to the binding agent.

27. An apparatus according to claim 23, further comprising a means for detecting binding of an analyte to the biding agent and wherein the detecting means is selected from fluorimetric, chemiluminescent, radiochemical, physical and colourimetric means.

28. An apparatus according to claim 23, further comprising a means for detecting binding of an analyte to the binding agent and wherein the detecting means comprises a photometric device capable of detecting and/or quantifying light emitted from porous membrane (b).

29. An apparatus according to claim 23, further comprising a means for detecting binding of an analyte to the binding agent and wherein the detecting means comprises a photometric device and the photometric device is a luminometer.

30. An apparatus according to claim 23, further comprising a means for detecting binding of an analyte to the binding agent and wherein the detecting means comprises imaging means.

31. An apparatus according to claim 23, wherein said at least one analyte-specific binding agent is a polynucleotide probe.

32. An apparatus according to claim 23, wherein said at least one analyte-specific binding agent is an Expressed Sequence Tag (EST).

33. An apparatus according to claim 23, wherein said at least one analyte-specific binding agent is a polypeptide binding agent.

34. An apparatus according to claim 23, wherein said at least one analyte-specific binding agent is an antibody or a fragment thereof.

35. An apparatus according to claim 23, wherein said at least one analyte-specific binding agent is immobilised directly or indirectly on said porous membrane.

36. An apparatus according to claim 23, wherein the or each first receptacle is positioned at least in part in a second receptacle which is capable of collecting liquid from the fluid outlet of the first receptacle such its porous membrane may be submerged in said liquid.

37. An apparatus for use in an assay comprising:
(a) at least one first receptacle comprising a fluid inlet and a fluid outlet;
(b) a porous membrane; and
(c) at least one analyte-specific binding agent,
characterized in that said at least one analyte-specific binding agent is immobilised on the underside of said porous membrane relative to the fluid inlet wherein a plurality of analyte-specific binding agents is immobilised on said porous membrane in the form of an array.

38. An apparatus according to claim 37, wherein the array comprises at least one control probe.

39. An apparatus according to claim 37, further comprising a means for drawing liquid from the at least one first receptacle through the fluid outlet.

40. An apparatus according to claim 37, further comprising a means for drawing liquid from the at least one first receptacle through the fluid outlet and wherein the drawing means is a vacuum pump.

41. An apparatus according to claim 37, further comprising a means for detecting binding of an analyte to the binding agent.

42. An apparatus according to claim 37, further comprising a means for detecting binding of an analyte to the biding agent and wherein the detecting means is selected from fluorimetric, chemiluminescent, radiochemical, physical and colourimetric means.

43. An apparatus according to claim 37, further comprising a means for detecting binding of an analyte to the binding agent and wherein the detecting means comprises a photometric device capable of detecting and/or quantifying light emitted from porous membrane (b).

44. An apparatus according to claim 37, further comprising a means for detecting binding of an analyte to the binding agent and wherein the detecting means comprises a photometric device and the photometric device is a luminometer.

45. An apparatus according to claim 37, further comprising a means for detecting binding of an analyte to the binding agent and wherein the detecting means comprises imaging means.

46. An apparatus according to claim 37, wherein said at least one analyte-specific binding agent is a polynucleotide probe.

47. An apparatus according to claim 37, wherein said at least one analyte-specific binding agent is an Expressed Sequence Tag (EST).

48. An apparatus according to claim 37, wherein said at least one analyte-specific binding agent is a polypeptide binding agent.

49. An apparatus according to claim 37, wherein said at least one analyte-specific binding agent is an antibody or a fragment thereof.

50. An apparatus according to claim 37, wherein said at least one analyte-specific binding agent is immobilised directly or indirectly on said porous membrane.

51. An apparatus according to claim 37, wherein the or each first receptacle is positioned at least in part in a second receptacle which is capable of collecting liquid from the fluid outlet of the first receptacle such its porous membrane may be submerged in said liquid.

* * * * *